US010179785B2

(12) United States Patent
Heo et al.

(10) Patent No.: US 10,179,785 B2
(45) Date of Patent: Jan. 15, 2019

(54) IMIDAZOTRIAZINONE OR IMIDAZOPYRAZINONE DERIVATIVES, AND USE THEREOF

(71) Applicant: ST PHARM CO., LTD., Siheung-si (KR)

(72) Inventors: Jung Nyoung Heo, Daejeon (KR); Hwan Jung Lim, Daejeon (KR); Kwang Rok Kim, Daejeon (KR); Kyung Jin Kim, Siheung-si (KR); Uk Il Kim, Siheung-si (KR); Hyung Tae Bang, Siheung-si (KR); Ji Hye Yoon, Siheung-si (KR)

(73) Assignee: ST PHARM CO., LTD., Siheung-si (KR)

( * ) Notice: Subject to any disclaimer, the term of this patent is extended or adjusted under 35 U.S.C. 154(b) by 0 days.

(21) Appl. No.: 15/325,692

(22) PCT Filed: Jul. 10, 2015

(86) PCT No.: PCT/KR2015/007220
§ 371 (c)(1),
(2) Date: Jan. 11, 2017

(87) PCT Pub. No.: WO2016/006975
PCT Pub. Date: Jan. 14, 2016

(65) Prior Publication Data
US 2017/0166572 A1 Jun. 15, 2017

(30) Foreign Application Priority Data

Jul. 11, 2014 (KR) .................. 10-2014-0087799
May 15, 2015 (KR) .................. 10-2015-0068368

(51) Int. Cl.
C07D 487/04 (2006.01)
C07D 403/04 (2006.01)
C07D 403/14 (2006.01)
C07D 401/04 (2006.01)
C07D 401/14 (2006.01)
A61K 31/53 (2006.01)
A61K 31/4985 (2006.01)
A61P 35/00 (2006.01)

(52) U.S. Cl.
CPC ........ C07D 487/04 (2013.01); A61K 31/4985 (2013.01); A61K 31/53 (2013.01); C07D 401/04 (2013.01); C07D 401/14 (2013.01); C07D 403/04 (2013.01); C07D 403/14 (2013.01)

(58) Field of Classification Search
CPC .. C07D 487/04; C07D 401/04; C07D 401/14; C07D 403/04; C07D 403/14; A61K 31/53; A61K 31/4985
USPC .......................... 544/184, 350; 514/243, 249
See application file for complete search history.

(56) References Cited

U.S. PATENT DOCUMENTS

2013/0331375 A1 12/2013 Haynes et al.
2013/0345215 A1 12/2013 Feng et al.
2013/0345226 A1 12/2013 Hermann et al.

FOREIGN PATENT DOCUMENTS

KR  10-2014-0051944 A   5/2014
WO  WO-2013/110768 A1   8/2013
WO  WO-2013/143663 A1  10/2013
WO  WO-2013/164061 A1  11/2013
WO  WO-2013/164061 A8  11/2013

OTHER PUBLICATIONS

Lehtio et al., FEBS Journal 280 (2013) 3576-3593.*
Cecil Textbook of Medicine, edited by Bennet, J.C., and Plum F., 20th edition,vol. 1, 1004-1010, 1996.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Bae J. et al., "Tankyrase 1 Interacts with Mcl-1 Proteins and Inhibits Their Regulation of Apoptosis", *J. Biol. Chem.*, (2003), 278: 5195-5204.
Chang W. et al., "NuMA is a major acceptor of poly(ADP-ribosyl)ation by tankyrase 1 in mitosis", *Biochem. J.*, (2005), 391:177-184.
Chen B. et al., "Small molecule-medicated disruption of Wnt-dependent signaling in tissue regeneration and cancer", *Nature Chemical Biology*, (2009), 5(2):100-107.
Chi N. et al., "Tankyrase Is a Golgi-associated Mitogen-activated Protein Kinase Substrate That Interacts with IRAP in GLUT4 Vesicles", *J. Biol. Chem.*, (2000), 275: 38437-38444.
Chiang, Y.J. et al., "Tankyrase 1 and Tankyrase 2 Are Essential but Redudant for Mouse Embryonic Development", *PLoS One*, (2008), 3(7): e2639.
Huang S.A. et al., "Tankyrase inhibition stabilizes axin and antagonizes Wnt signaling", *Nature*, (2009), 461:614-620.
Liu W. et al., "Mutations in AXIN2 cause colorectal cancer with defective mismatch repair by activating β-catenin/ TCF signaling", *Nat. Genet.*, (2000), 26: 146-147.
Miyaki M. et al. "Characteristics of Somatic Mutation of the Adenomatous Polyposis Coli Gene in Colorectal Tumors", *Cancer Res.*, (1994) 54:3011-3020.
Schreiber V. et al., "Poly(ADP-ribose): novel functions for an old molecule", *Nature Reviews Molecular Cell Biology*, 7:517-528.
Taniguchi K. et al. "Mutational spectrum of β-catenin, AXIN1, and AXIN2 in hepatocellular carcinomas and hepatoblastomas", *Oncogene*, (2002) 21:4863-4871.

(Continued)

Primary Examiner — Venkataraman Balasubramanian
(74) Attorney, Agent, or Firm — Morrison & Foerster LLP

(57) ABSTRACT

The present invention relates to a novel imidazotriazinone or imidazopyrazinone derivative, a tautomer thereof, a stereoisomer thereof and their mixture, or a pharmaceutically acceptable salt thereof; and a pharmaceutical composition for preventing or treating a tankyrase-related disease, which contains the same as an active ingredient.

9 Claims, No Drawings

(56) References Cited

OTHER PUBLICATIONS

Waaler J. et al., "A Novel Tankyrase Inhibitor Decreases Canonical Wnt Signaling in Colon Carcinoma Cells and Reduces Tumor Growth in Conditional APC Mutant Mice", *Cancer Res.*, (2012) 72(11):2822-2832.

Wahlbert E. et al., "Family-wide chemical profiling and structural analysis or PARP and tankyrase inhibitors", *Nat. Biotechnol*, (2012),30(3):283-288.

\* cited by examiner

IMIDAZOTRIAZINONE OR IMIDAZOPYRAZINONE DERIVATIVES, AND USE THEREOF

CROSS-REFERENCE TO RELATED APPLICATIONS

This application is a U.S. national phase application under 35 U.S.C. § 371 of International Application No. PCT/KR2015/007220, filed on Jul. 10, 2015, which claims the priority benefit of Korean Patent Application No. 10-2014-0087799, filed on Jul. 11, 2014, and Korean Patent Application No. 10-2015-0068368, filed on May 15, 2015, the disclosures of all of which are hereby incorporated by reference in their entirety.

TECHNICAL FIELD

The present invention relates to a novel imidazotriazinone or imidazopyrazinone derivative, a tautomer thereof, a stereoisomer thereof and their mixture, or a pharmaceutically acceptable salt thereof; and a pharmaceutical composition for preventing or treating a tankyrase-related disease, which contains the same as an active ingredient.

BACKGROUND ART

Human tankyrase belongs to the family of poly(ADP-ribose) polymerase (PARP) proteins which consists of 17 members that share a catalytic PARP domain. PARPs constitute a family of cell signaling enzymes present in eukaryotes which catalyze poly(ADP-ribosylation) (PARsylation) of DNA-binding proteins and other substrate proteins. PARPs are also known as poly(ADP-ribose) synthases or poly(ADP-ribose) transferases (pARTs). Some PARPs also transfer single ADP-ribosyl-moieties. These enzymes, for example, play an important role in the immediate cellular response to DNA damage. In response to DNA damage induced by ionizing radiation, oxidative stress and DNA-binding anti-tumor drugs, PARPs add ADP-ribose units to the carboxylate groups of aspartic and glutamic residues of target proteins. This poly(ADP-ribosylation) is a post-translational modification process that triggers the inactivation of the acceptor protein through the attachment of a complex branched by a polymer of ADP-ribose units. ADP ribosylation is a post-translational protein modification process in which the ADP-ribose moiety is transferred from NAD onto specific amino acid side chains of target proteins (Schreiber et al., 2006, *Nature Reviews Cell Biology*, 7: 517-528).

PARP family proteins are promising therapeutic targets. PARP1 and PARP2 play a role in DNA damage responses and PARP inhibitors sensitize cancer cells for drug and radiation therapies. In addition, PARP1 has been linked to other diseases including inflammation, neuronal cell death and ischemia. Tankyrases (TNKS1 and TNKS2), which share high sequence similarity with PARP1, are also emerging therapeutic targets. Tankyrases were initially known as regulators of telomerase activity and are involved in DNA damage responses and Wnt signaling (Wahlbert et al., 2012, *Nat. Biotechnol.*, 30(3): 283-288).

The tankyrase protein family consists of tankyrase 1 (TNKS1) and tankyrase 2 (TNKS2) which share 85% amino acid identity. Biological functions of both tankyrase 1 and tankyrase 2 were studied in genetically engineered mice lacking mouse tankyrase 1 and/or tankyrase 2. Tankyrase 2-deficient mice developed normally and showed no detectable change in telomere length, but did show a significant decrease in total body weight that might reflect a role of tankyrase 2 in glucose or fat metabolism. No defects in telomere length maintenance were detected in tankyrase 1-deficient mice. However, in double-knockout mice lacking both tankyrase 1 and tankyrase 2 embryonic lethality was observed on embryonic day 10 (Chiang et al., 2008, *PLoS One*, 3(7): e2639).

A key feature of the Wnt/β-catenin pathway is the regulated proteolysis of the downstream effector β-catenin by the β-catenin destruction complex. The principal constituents of a β-catenin destruction complex are adenomatous polyposis coli (APC), axin and GSK3α/β. In the absence of Wnt pathway activation, cytosolic β-catenin is constitutively phosphorylated and targeted for degradation. Upon Wnt stimulation, a β-catenin destruction complex is dissociated, which leads to accumulation of β-catenin in the nucleus and transcription of Wnt pathway responsive genes.

It has been recently found that, in the Wnt/β-catenin pathway, a tankyrase inhibitor selectively inhibits the transcription mediated by β-catenin by promoting β-catenin degradation through stabilization of axin (Huang et al., 2009, *Nature*, 461(7264): 614-620).

Inappropriate activation of the pathway, mediated by overexpression of Wnt proteins or mutations affecting the components of the β-catenin destruction complex, thus leading to stabilization of β-catenin, has been observed in many cancers, for example, colon cancer, gastric cancer, hepatocellular carcinoma, breast cancer, medulloblastoma, melanoma, non-small cell lung cancer, pancreatic adenocarcinoma and prostate cancer (Waaler et al., 2012, *Cancer Res.*, 72(11): 2822-2832). Notably, truncating mutations of a tumor suppressor APC are the most prevalent genetic alterations in colorectal carcinomas (Miyaki et al., 1994, *Cancer Res.*, 54: 3011-3020). In addition, Axin1 and Axin2 mutations have been identified in patients with hepato-carcinomas and colorectal carcinomas (Taniguchi et al., 2002, *Oncogene*, 21: 4863-4871; Liu et al., 2000, *Nat. Genet.*, 26: 146-147). These somatic mutations result in Wnt-independent stabilization of β-catenin and constitutive activation of β-catenin-mediated transcription. Furthermore, deregulated Wnt pathway activity has also been implicated in many other non-cancer diseases including osteoporosis, osteoarthritis, polycystic kidney disease, pulmonary fibrosis, diabetes, schizophrenia, vascular diseases, cardiac diseases, non-oncogenic proliferative diseases, neurodegenerative diseases such as Alzheimer's disease, etc.

Therapeutics which are directed to and can correct dysregulation of the Wnt signaling pathway have been implicated in conditions such as bone density defects, coronary disease, late-onset Alzheimer's disease, familial exudative vitreoretinopathy, retinal angiogenesis, tetraamelia, Muellerian-duct regression and virilization, Serkal syndrome, type 2 diabetes, Fuhrmann syndrome, skeletal dysplasia, focal dermal hypoplasia and neural tube defects. Although the introduction has focused on the relevance of Wnt signaling in cancer, the Wnt signaling pathway is of fundamental importance in a broad range of human diseases, not necessarily being limited to the examples provided above for illustrative purposes.

Meanwhile, it has recently been reported that intracellular axin levels are influenced by poly(ADP-ribose) polymerase family members tankyrase-1 and tankyrase-2 (also known as PARP5a and PARP5b) (*Nature Chemical Biology*, 2009, 5: 100; *Nature*, 2009, 461: 614). The tankyrase enzymes are able to poly-ADP ribosylate (PARsylate) axin, which marks this protein for subsequent ubiquitination and proteasomal degradation. Thus, it would be expected that in the presence of an inhibitor of tankyrase catalytic activity, the axin protein concentration would be increased, resulting in higher concentration of the destruction complex, decreased concentration of unphosphorylated intracellular β-catenin and decreased Wnt signaling. An inhibitor of tankyrase-1 and -2 would also be expected to have an effect on other biological functions of tankyrase proteins (e.g., chromosome end (telomere) protection, insulin responsiveness and spindle assembly during mitosis) (Chang et al., 2005, *Biochem. J.*, 391: 177-184; Chi et al., 2000, J. Biol. Chem., 275: 38437-38444; Bae et al., 2003, *J. Biol. Chem.*, 278: 5195-5204).

DISCLOSURE OF INVENTION

Technical Problem

There are consistent needs for novel therapeutic agents that can be used for cancers and hyperproliferative conditions. Therefore, the inventors of the present invention have researched to design and develop novel pharmaceutical compounds that can inhibit or modulate the activity of tankyrase enzymes which are members of PARP family and regulate Wnt activity. As a result, they have found that the newly designed and synthesized imidazotriazinone or imidazopyrazinone derivatives represented by Chemical Formula 1 can inhibit or regulate tankyrase activity and have completed the present invention:

[Chmeical Formula 1]

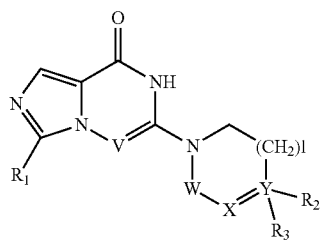

Solution to Problem

In an aspect, the present invention provides a compound represented by Chemical Formula 1, a tautomer thereof, a stereoisomer thereof and their mixture, or a pharmaceutically acceptable salt thereof:

[Chemical Formula 1]

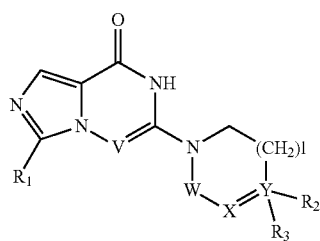

wherein
V is N or CH;
$R_1$ is hydrogen, $C_{1-6}$ alkyl, $C_{1-6}$ hydroxyalkyl, or $C_{1-6}$ dihydroxyalkyl;
each of W and X is independently $CHR_4$ or CO;
Y is N or C;

═══ is a single bond or a double bond, determined by X and Y;
l is 0, 1 or 2;
$R_2$ is none, hydrogen, hydroxyl, cyano or $C_{1-6}$ alkyl;
$R_3$ is

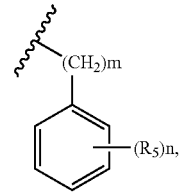

heteroaryl-$C_{1-3}$ alkyl, heterocyclyl, or heterocyclyl $C_{1-3}$ alkyl;
$R_4$ is none, hydrogen, hydroxyl, $C_{1-6}$ alkyl or amine;
m is 0, 1, 2 or 3;
n is 0, 1, 2, 3, 4 or 5;
each of $R_5$ is independently halo, $C_{1-6}$ alkyl, $C_{2-6}$ alkenyl, $C_{1-6}$ alkoxy, $C_{1-3}$ alkoxy-$C_{1-3}$ alkyl, $C_{1-6}$ hydroxyalkyl, $C_{1-6}$ dihydroxyalkyl, $C_{1-6}$ haloalkyl unsubstituted or optionally substituted with hydroxy, $C_{3-7}$ cycloalkyl, $C_{1-6}$ alkyloxo, cyano, nitro, carboxy, $C_{1-6}$ alkoxycarbonyl or —Z—$(CH_2)_p$—$R_6$;
p is 0, 1, 2, 3, 4, 5 or 6;
Z is —O—, —S(O)$_q$—, —NR$_7$—, —CONR$_7$—, —CHR$_7$— or none;
q is 0, 1 or 2;
$R_6$ is hydrogen, cyano, hydroxyl, azido, $C_{1-6}$ alkoxy, $C_{1-3}$ alkoxy-$C_{1-3}$ alkyl, $C_{5-10}$ aryl, carboxy, $C_{1-6}$ dihydroxyalkyl, $C_{1-6}$ alkyl, $C_{1-6}$ haloalkyl unsubstituted or optionally substituted with hydroxy, $C_{3-6}$ cycloalkyl, heterocyclyl, heteroaryl, —S(O)$_r$—R$_8$, —O—(C═O)—R$_8$, —(C═O)—R$_8$, —OR$_8$, —COOR$_8$, —NR$_9$R$_{10}$ or —(C═O)NR$_9$R$_{10}$;
r is 0, 1 or 2;
$R_7$ is hydrogen, $C_{1-6}$ alkyl, $C_{3-6}$ cycloalkyl, $C_{1-3}$ alkyl-$C_{3-6}$ cycloalkyl or $C_{1-3}$ alkoxy-$C_{1-3}$ alkyl;
$R_8$ is hydrogen, $C_{1-6}$ alkyl, $C_{1-6}$ alkoxy, amino, $C_{1-6}$ alkylamino, $C_{1-6}$ aminoalkyl, heterocyclyl, $C_{3-6}$ cycloalkyl, $C_{1-3}$ alkyl-$C_{3-6}$ cycloalkyl, $C_{1-6}$ alkyloxo or $C_{1-3}$ alkoxy-$C_{1-3}$ alkyl;
each of $R_9$ and $R_{10}$ is independently hydrogen, $C_{1-6}$ alkyl, $C_{1-6}$ alkoxy, $C_{3-6}$ cycloalkyl, $C_{1-3}$ alkyl-$C_{3-6}$ cycloalkyl, $C_{1-3}$ alkoxy-$C_{1-3}$ alkyl or —(SO$_2$)—$C_{1-3}$ alkyl;
each of the heteroaryls may be a 5- to 10-membered single or fused ring containing one or more heteroatom selected from the group consisting of N, O, S and a combination thereof, and each of the heterocycles may be a 3- to 10-membered single or fused ring containing one or more heteroatom selected from the group consisting of N, O, S and a combination thereof;
each of the cycloalkyls and heterocyclyls may optionally be substituted with one to three substituents selected from the group consisting of $C_{1-6}$ alkyl, hydroxyl, oxo, $C_{1-6}$ hydroxyalkyl, halo, cyano, nitro, $C_{1-6}$ haloalkyl, $C_{1-6}$ alkoxy, formyl, $C_{1-6}$ alkylformyl, carboxy, $C_{1-6}$ alkylcarboxy, amino, $C_{1-6}$ alkylamino, di($C_{1-6}$ alkyl)amino, carbamoyl, $C_{1-6}$ alkylcarbamoyl, di($C_{1-6}$ alkyl)carbamoyl and $C_{1-3}$ alkoxy-$C_{1-3}$ alkyl; and
each of the aryls and heteroaryls may optionally be substituted with one to three substituents selected from the group consisting of $C_{1-6}$ alkyl, $C_{1-6}$ alkoxy, $C_{1-3}$ alkoxy-$C_{1-3}$ alkyl, $C_{1-6}$ hydroxyalkyl, $C_{1-6}$ haloalkyl, halo, cyano, pyrazinyl, hydroxy, oxo, nitro, formyl, $C_{1-6}$ alkylformyl, carboxy, $C_{1-6}$ alkylcarboxy, amino, $C_{1-6}$ alkylamino, di($C_{1-6}$ alkyl) amino, carbamoyl, $C_{1-6}$ alkylcarbamoyl, di($C_{1-6}$ alkyl)carbamoyl and $C_{1-6}$ alkylsulfonyl.

Preferably, in Chemical Formula 1,
V is N or CH;
$R_1$ is hydrogen, $C_{1-6}$ alkyl, $C_{1-6}$ hydroxyalkyl, or $C_{1-6}$ dihydroxyalkyl;
each of W and X is independently CH or $CH_2$;
Y is N or C;
═══ is a single bond or a double bond; and
l is 0, 1 or 2.

Preferably, in Chemical Formula 1,
V is N or CH;
$R_1$ is hydrogen or $C_{1-6}$ alkyl;
each of W and X is independently CH or $CH_2$;
Y is N or C;
═══ is a single bond or a double bond;
l is 0, 1 or 2;
$R_2$ is none, hydrogen or hydroxyl;
$R_3$ is

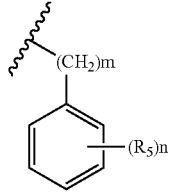

or heteroaryl;
$R_4$ is none or hydrogen;
m is 0;
n is 1, 2 or 3;
each of $R_5$ is independently halo, $C_{2-6}$ alkenyl, $C_{1-6}$ alkoxy, $C_{1-3}$ alkoxy-$C_{1-3}$ alkyl, $C_{1-6}$ hydroxyalkyl, $C_{1-6}$ dihydroxyalkyl or —Z—$(CH_2)_p$—$R_6$;
p is 0, 1, 2, 3 or 5;
Z is —O—, —$NR_7$— or none;
$R_6$ is cyano, hydroxyl, azido, $C_{1-6}$ alkoxy, $C_{1-3}$ alkoxy-$C_{1-3}$ alkyl, $C_{5-10}$ aryl, carboxy, $C_{1-6}$ dihydroxyalkyl, $C_{1-6}$ haloalkyl unsubstituted or optionally substituted with hydroxy, heterocyclyl, heteroaryl, —S(O)$_r$—$R_8$, —O—(C═O)—$R_8$, —(C═O)—$R_8$, —$NR_9R_{10}$ or —(C═O)$NR_9R_{10}$;
r is 2;
$R_7$ is hydrogen;
$R_8$ is hydrogen, $C_{1-6}$ alkyl, $C_{1-6}$ alkoxy, amino, $C_{1-6}$ alkylamino, $C_{1-6}$ aminoalkyl or heterocyclyl;
each of $R_9$ and $R_{10}$ is independently hydrogen, $C_{1-6}$ alkyl, $C_{1-3}$ alkoxy-$C_{1-3}$ alkyl or —(SO$_2$)—$C_{1-3}$ alkyl;
each of the heteroaryls may be a 5- to 10-membered single or fused ring containing one or more heteroatom selected from the group consisting of N, O, S and a combination thereof, and each of the heterocycles may be a 3- to 10-membered single or fused ring containing one or more heteroatom selected from the group consisting of N, O, S and a combination thereof;
each of the heterocyclyls may optionally be substituted with one to three substituents selected from the group consisting of $C_{1-6}$ alkyl, hydroxyl, amino, oxo, $C_{1-6}$ hydroxyalkyl and halo; and
each of the heteroaryls may optionally be substituted with one to three $C_{1-6}$ alkyl.

Preferably, in Chemical Formula 1,
V is N or CH;

$R_1$ is hydrogen or methyl;
each of W and X is independently CH or $CH_2$;
Y is N or C;
═══ is a single bond or a double bond;
l is 1 or 2;
$R_2$ is none, hydrogen or hydroxyl;
$R_3$ is

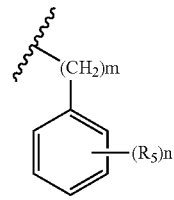

or heteroaryl;
$R_4$ is none or hydrogen;
m is 0;
n is 1, 2 or 3;
each of $R_5$ is independently fluoro, vinyl, isopropoxy, methoxyethyl, methoxypropyl, hydroxyethyl, 1,2-dihydroxyethyl, 2,3-dihydroxypropyl or —Z—$(CH_2)_p$—$R_6$;
p is 0, 1, 2, 3 or 5;
Z is —O—, —$NR_7$— or none;
$R_6$ is cyano, hydroxyl, azido, methoxy, ethoxy, methoxyethyl, $C_{5-10}$ aryl, carboxy, 1,2-dihydroxyethyl, 1-chloro-3-hydroxyisopropyl, perfluoromethyl, heterocyclyl, heteroaryl, —S(O)$_r$—$R_8$, —O—(C═O)—$R_8$, —(C═O)—$R_8$, —$NR_9R_{10}$ or —(C═O)$NR_9R_{10}$;
r is 2;
$R_7$ is hydrogen;
$R_8$ is hydrogen, methyl, amino, methylamino, or aminoethyl;
each of $R_9$ and $R_{10}$ is independently hydrogen, methyl, ethyl or methoxyethyl;
each of the heteroaryls may be a 5- to 10-membered single or fused ring containing one or more heteroatom selected from the group consisting of N, O, S and a combination thereof, and each of the heterocycles may be a 3- to 10-membered single or fused ring containing one or more heteroatom selected from the group consisting of N, O, S and a combination thereof;
each of the heterocyclyls may optionally be substituted with one to three substituents selected from the group consisting of methyl, fluoro, hydroxyl, amino and oxo; and
each of the heteroaryls may optionally be substituted with one to three methyl.

Preferably, in Chemical Formula 1,
each of the aryls is phenyl or naphthyl;
each of the heteroaryls may be selected from the group consisting of tetrazolyl, imidazolyl, pyridinyl, pyridazinyl, pyrimidyl, triazinyl, pyrrolyl, pyrazolyl, triazolyl, pyrazinyl, furyl, thienyl, isoxazolyl, thiazolyl, isothiazolyl, thiadiazolyl, furazanyl, oxazolyl, indolyl, isoindolyl, indazolyl, quinolinyl, isoquinolinyl, benzothiazolyl, benzoxazolyl, benzofuranyl, benzoimidazolyl, benzotriazolyl and azaindolyl; and
each of the heterocyclyls may be selected from the group consisting of tetrahydropyranyl, tetrahydrofuranyl, dihydrofuranyl, dihydropyranyl, dioxanyl, dithianyl, dioxolanyl, imidazolidinyl, imidazolinyl, pyrrolinyl, oxetanyl, pyrrolidinyl, piperidinyl, piperazinyl, morpholinyl, thiomorpholinyl, dioxothiomorpholinyl, dioxotetrahydrothiophenyl, dioxothiolanyl, oxopiperidinyl, oxopyrrolidinyl and oxo-oxazolidinyl.

Preferably, in Chemical Formula 1,
each of the aryls is phenyl;
each of the heteroaryls is tetrazolyl or imidazolyl; and
each of the heterocyclyls is tetrahydrofuranyl, oxetanyl, pyrrolidinyl, piperidinyl, piperazinyl or morpholinyl.

Preferably, in Chemical Formula 1,
each of the heterocyclyls is tetrahydrofuranyl, oxetanyl, pyrrolidinyl, piperidinyl, piperazinyl, morpholinyl, 4-methylpiperazinyl, 4-methyl-2-oxopiperazinyl, 3-hydroxypyrrolidinyl, 2-hydroxymethylpyrrolidinyl, N-methylpyrrolidinyl, 4-hydroxypiperidinyl, 4-hydroxy-4-methylpiperidinyl, 4-aminopiperidinyl, 2-oxopiperidinyl, 2,6-dimethylpiperidinyl or 4,4-difluoropiperidinyl.

More Preferably, the compound may be
1) 2-(4-(2-fluorophenyl)piperazin-1-yl)-7-methylimidazo[1,5-f][1,2,4]triazin-4(3H)-one,
2) 2-(4-(2,6-difluoro-4-(2-methoxyethoxy)phenyl)piperazin-1-yl)-7-methylimidazo[1,5-f][1,2,4]triazin-4(3H)-one,
3) 2-(4-(4-(benzyloxy)-2,6-difluorophenyl)piperazin-1-yl)-7-methylimidazo[1,5-f][1,2,4]triazin-4(3H)-one,
4) 2-(4-(2,6-difluoro-4-(2-morpholinoethoxy)phenyl)piperazin-1-yl)-7-methylimidazo[1,5-f][1,2,4]triazin-4(3H)-one,
5) 2-(4-(2,6-difluoro-4-(2-(piperidin-1-yl)ethoxy)phenyl)piperazin-1-yl)-7-methylimidazo[1,5-f][1,2,4]triazin-4(3H)-one,
6) 2-(4-(4-(2-(dimethylamino)ethoxy)-2,6-difluorophenyl)piperazin-1-yl)-7-methylimidazo[1,5-f][1,2,4]triazin-4(3H)-one,
7) 2-(4-(2,6-difluoro-4-(2-hydroxyethoxy)phenyl)piperazin-1-yl)-7-methylimidazo[1,5-f][1,2,4]triazin-4(3H)-one,
8) (S)-2-(3,5-difluoro-4-(4-(7-methyl-4-oxo-3,4-dihydroimidazo[1,5-f][1,2,4]triazin-2-yl) piperazin-1-yl)phenoxy)ethyl 2-aminopropanoate hydrochloride,
9) 2-(4-(4-(2,3-dihydroxypropoxy)-2,6-difluorophenyl)piperazin-1-yl)-7-methylimidazo[1,5-f][1,2,4]triazin-4(3H)-one,
10) 2-(4-(2,6-difluoro-4-(morpholinomethyl)phenyl)piperazin-1-yl)-7-methylimidazo[1,5-f][1,2,4]triazin-4(3H)-one,
11) 2-(4-(2,6-difluoro-4-((4-methylpiperazin-1-yl)methyl)phenyl)piperazin-1-yl)-7-methylimidazo[1,5-f][1,2,4]triazin-4(3H)-one,
12) 2-(4-(2,6-difluoro-4-(oxetan-3-yloxy)phenyl)piperazin-1-yl)-7-methylimidazo[1,5-f][1,2,4]triazin-4(3H)-one,
13) 2-(4-(2,6-difluoro-4-(1-hydroxyethyl)phenyl)piperazin-1-yl)-7-methylimidazo[1,5-f][1,2,4]triazin-4(3H)-one,
14) 2-(4-(2,6-difluoro-4-(1-methoxyethyl)phenyl)piperazin-1-yl)-7-methylimidazo[1,5-f][1,2,4]triazin-4(3H)-one,
15) 2-(4-(2,6-difluorophenyl)piperazin-1-yl)-7-methylimidazo[1,5-f][1,2,4]triazin-4(3H)-one,
16) 2-(4-(2,4,6-trifluorophenyl)piperazin-1-yl)-7-methylimidazo[1,5-f][1,2,4]triazin-4(3H)-one,
17) 2-(4-(2,6-difluoro-4-(2-methoxyethoxy)phenyl)-4-hydroxypiperidin-1-yl)-7-methylimidazo[1,5-f][1,2,4]triazin-4(3H)-one,
18) 2-(4-(2,6-difluoro-4-(2-methoxyethylamino)phenyl)piperazin-1-yl)-7-methylimidazo[1,5-f][1,2,4]triazin-4(3H)-one,
19) 2-(4-(2,6-difluoro-4-(((2-methoxyethyl)(methyl)amino)methyl)phenyl)piperazin-1-yl)-7-methylimidazo[1,5-f][1,2,4]triazin-4(3H)-one,
20) 2-(4-(4-(1,2-dihydroxyethyl)-2,6-difluorophenyl)piperazin-1-yl)-7-methylimidazo[1,5-f][1,2,4]triazin-4(3H)-one,
21) 2-(4-(4-(2,3-dihydroxypropyl)-2,6-difluorophenyl)piperazin-1-yl)-7-methylimidazo[1,5-f][1,2,4]triazin-4(3H)-one,
22) 2-(4-(1H-tetrazol-5-yl)piperidin-1-yl)-7-methylimidazo[1,5-f][1,2,4]triazin-4(3H)-one,
23) 7-methyl-2-(4-(2-methyl-2H-tetrazol-5-yl)piperidin-1-yl)imidazo[1,5-f][1,2,4]triazin-4(3H)-one,
24) 2-(4-(2,6-difluoro-4-(2-(pyrrolidin-1-yl)ethoxy)phenyl)piperazin-1-yl)-7-methylimidazo[1,5-f][1,2,4]triazin-4(3H)-one,
25) 2-(4-(2,6-difluoro-4-(2-(4-methylpiperazin-1-yl)ethoxy)phenyl)piperazin-1-yl)-7-methylimidazo[1,5-f][1,2,4]triazin-4(3H)-one,
26) 2-(4-(2,6-difluoro-4-(3-(piperidin-1-yl)propoxy)phenyl)piperazin-1-yl)-7-methylimidazo[1,5-f][1,2,4]triazin-4(3H)-one,
27) 2-(4-(4-(bis(2-methoxyethyl)amino)-2,6-difluorophenyl)piperazin-1-yl)-7-methylimidazo[1,5-f][1,2,4]triazin-4(3H)-one,
28) 2-(4-(2,6-difluoro-4-(2-oxo-2-(piperidin-1-yl)ethoxy)phenyl)piperazin-1-yl)-7-methylimidazo[1,5-f][1,2,4]triazin-4(3H)-one,
29) 2-(4-(2,6-difluoro-4-(2-oxo-2-(pyrrolidin-1-yl)ethoxy)phenyl)piperazin-1-yl)-7-methylimidazo[1,5-f][1,2,4]triazin-4(3H)-one,
30) 2-(4-(4-(2-(4-aminopiperidin-1-yl)ethoxy)-2,6-difluorophenyl)-1,4-diazepan-1-yl)-7-methylimidazo[1,5-f][1,2,4]triazin-4(3H)-one,
31) 2-(4-(4-(2-azidoethoxy)-2,6-difluorophenyl)piperazin-1-yl)-7-methylimidazo[1,5-f][1,2,4]triazin-4(3H)-one,
32) 2-(4-(4-(2-aminoethoxy)-2,6-difluorophenyl)piperazin-1-yl)-7-methylimidazo[1,5-f][1,2,4]triazin-4(3H)-one,
33) 2-(4-(2,6-difluoro-4-(2-(4-methyl-2-oxopiperazin-1-yl)ethoxy)phenyl)piperazin-1-yl)-7-methylimidazo[1,5-f][1,2,4]triazin-4(3H)-one,
34) 2-(4-(4-(2-(4-aminopiperidin-1-yl)ethoxy)-2,6-difluorophenyl)piperazin-1-yl)-7-methylimidazo[1,5-f][1,2,4]triazin-4(3H)-one,
35) 2-(4-(2,6-difluoro-4-(2-(3-hydroxypyrrolidin-1-yl)ethoxy)phenyl)piperazin-1-yl)-7-methylimidazo[1,5-f][1,2,4]triazin-4(3H)-one,
36) 2-(4-(2,6-difluoro-4-(2-(4-hydroxypiperidin-1-yl)ethoxy)phenyl)piperazin-1-yl)-7-methylimidazo[1,5-f][1,2,4]triazin-4(3H)-one,
37) 6-(4-(2,6-difluoro-4-(2-methoxyethoxy)phenyl)piperazin-1-yl)-3-methylimidazo[1,5-a]pyrazin-8(7H)-one,
38) 6-(4-(2,6-difluoro-4-(2-morpholinoethoxy)phenyl)piperazin-1-yl)-3-methylimidazo[1,5-a]pyrazin-8(7H)-one,
39) 6-(4-(2,6-difluoro-4-(2-(piperidin-1-yl)ethoxy)phenyl)piperazin-1-yl)-3-methylimidazo[1,5-a]pyrazin-8(7H)-one,
40) 6-(4-(4-(2-(dimethylamino)ethoxy)-2,6-difluorophenyl)piperazin-1-yl)-3-methylimidazo[1,5-a]pyrazin-8(7H)-one,
41) 6-(4-(2,6-difluoro-4-(morpholinomethyl)phenyl)piperazin-1-yl)-3-methylimidazo[1,5-a]pyrazin-8(7H)-one,
42) 6-(4-(2,6-difluoro-4-((4-methylpiperazin-1-yl)methyl)phenyl)piperazin-1-yl)-3-methylimidazo[1,5-a]pyrazin-8(7H)-one,
43) 6-(4-(2,6-difluoro-4-(oxetan-3-yloxy)phenyl)piperazin-1-yl)-3-methylimidazo[1,5-a]pyrazin-8(7H)-one,
44) 6-(4-(2,6-difluoro-4-(1-methoxyethyl)phenyl)piperazin-1-yl)-3-methylimidazo[1,5-a]pyrazin-8(7H)-one, 45) 6-(4-(2,6-difluoro-4-(((2-methoxyethyl)(methyl)amino)methyl)phenyl)piperazin-1-yl)-3-methylimidazo[1,5-a]pyrazin-8(7H)-one,
46) 6-(4-(2,6-difluoro-4-(2-(pyrrolidin-1-yl)ethoxy)phenyl)piperazin-1-yl)-3-methylimidazo[1,5-a]pyrazin-8(7H)-one,
47) 6-(4-(2,6-difluoro-4-(2-(4-methylpiperazin-1-yl)ethoxy)phenyl)piperazin-1-yl)-3-methylimidazo[1,5-a]pyrazin-8(7H)-one, or
48) 6-(4-(2,6-difluoro-4-(3-(piperidin-1-yl)propoxy)phenyl)piperazin-1-yl)-3-methylimidazo[1,5-a]pyrazin-8(7H)-one.

For example, the compound of the present invention may be prepared by synthesizing an imidazotriazinone derivative as an intermediate which serves as the core parent structure from a starting material, ethyl bromopyruvate, via a series of reactions and then introducing additional substituent by a substitution reaction using a reactive chloride group. The following reaction scheme is presented as an exemplary preparation method of the compound of the present invention. However, the method for preparing the compound of the present invention is not limited thereto and a method known in the art may be employed with appropriate modification, if necessary.

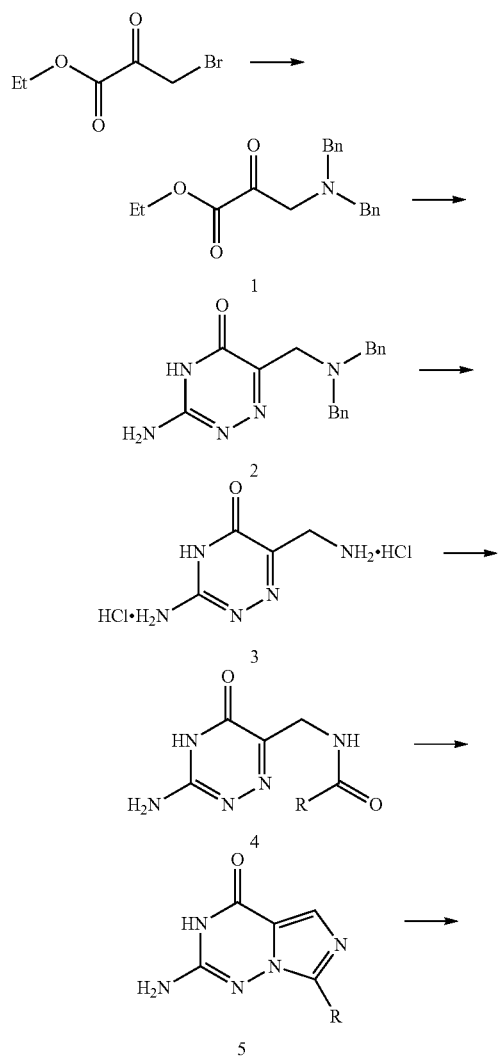

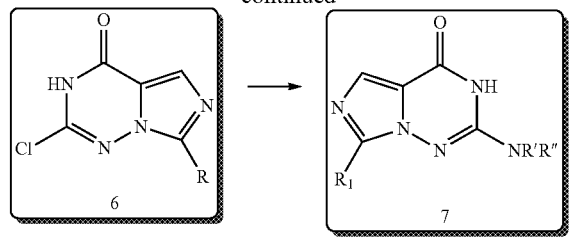

In the reaction scheme, $R_1$ is as defined in Chemical Formula 1.

First, after forming an aminopyruvate derivative (2) by reacting ethyl bromopyruvate with dibenzylamine, the formed aminopyruvate derivative was reacted with aminoguanidine bicarbonate (IUPAC name: hydrazinecarboximidamide carbonate) or 2-aminoacetimidamid bicarbonate to form a triazinone ring (2). Then, via hydrosoluble elimination reaction using a palladium catalyst, a benzyl group was eliminated from the product by hydrogenation. Here, the product was formed in the form of a hydrocholoride salt (3). Further, through a reaction with an active ester compound, the product was amidated (4). Preferably, the active ester compound may be $C_{1-7}$ alkanoic anhydride, $C_{2-7}$ hydroxyalkanoic anhydride, $C_{2-7}$ dehydroxyalkanoic anhydride, 1,1-dioxotian-4-carboxylic anhydride, or tetrahydropyran-4-carboxylic anhydride. More preferably, the active ester compound is $C_{1-7}$ alkanoic anhydride, although not limited thereto. Then, the product may form a compound with a structure of imidazotriazinone (5) which serves as the parent structure of the present invention via a cyclization reaction by $POCl_3$. Here, the product contains an amino group substituted into a triazinone ring and may be reacted with a chlorine-containing compound in the presence of tert-butyl nitrite (TBN) to replace the amino group with highly reactive chloride. The substitution reaction which replaces the amino group with chloride may be performed by reacting with pyridine hydrochloride using dichloromethane as a solvent or reacting with antimony trichloride using 1,2-dichloroethane as a solvent in the presence of TBN. Preferably, reacting with antimony trichloride using 1,2-dichloroethane as a solvent in the presence of TBN may be performed at a higher yield, but is not limited thereto. Additional amination reaction can be performed to the imidazotriazinone derivative substituted with chloro group (6) to obtain a target compound of the present invention, imidazotriazinone derivative (7). For example, the amination reaction can be accomplished by reaction of an amine compound comprising a suitable substituent for a desired target compound with DIPEA at 150° C. for 0.5 hour in an alcohol solvent such as isopropanol or ethanol.

Alternatively, the compound of the present invention may be prepared by synthesizing an imidazopyrazinone derivative, an intermediate which constitutes the core parent structure of the compound of the present invention, from 2,6-dichloropyrazine as a starting material, and then introducing additional substituent(s) through substitution reaction at reactive chloro group by a series of reactions described below. However, the method for preparing the compound of the present invention is not limited thereto and a method known in the art may be employed with appropriate modification, if necessary.

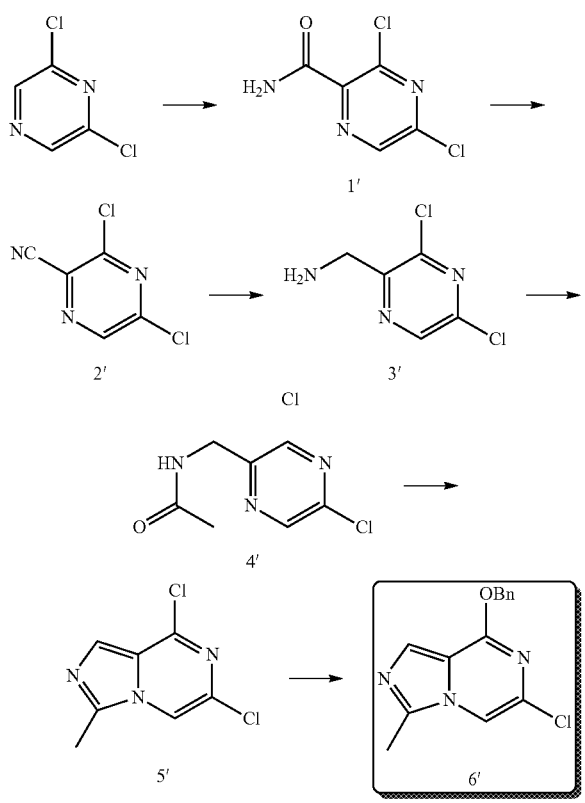

After the intermediate (6'), which constitutes the parent structure of the compound of the present invention, is synthesized as described above, a substituent replacing a chloro group is introduced by further carrying out one or more reactions known in the art.

For example, when the substituent introduced to replace to the chloro group is an amine group, the triazolopyridinone derivative compound (8') as the target compound of the present invention may be obtained from the intermediate compound (6') by conducting amination according to the following reaction scheme and, optionally, carrying out deprotection following the amination if necessary.

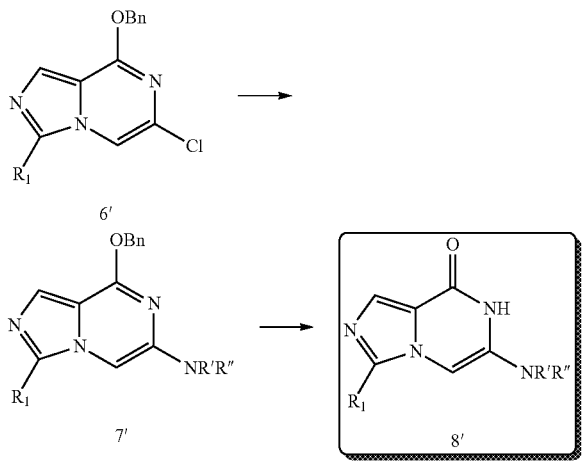

Preferably, the amination may be conducted via Buchwald reaction of the intermediate to react with an amine compound containing a substituent suitable for the desired target compound, in a dioxane or toluene solvent. Preferably, the reaction may be carried out at 110° C. for 12 to 24 hours.

Preferably, the deprotection may be accomplished by reaction in methanol solvent under 10% Pd/C catalyst to remove a benzyl group.

In another aspect, the present invention provides a pharmaceutical composition for treating or preventing a tankyrase-related disease, which contains the compound of the present invention, a tautomer thereof, a stereoisomer thereof and their mixture or a pharmaceutically acceptable salt thereof as an active ingredient.

Preferably, the compound of the present invention, the tautomer thereof, a stereoisomer thereof and their mixture, or the pharmaceutically acceptable salt thereof may exhibit activity of inhibiting activities of tankyrase 1, tankyrase 2 or both. Preferably, a pharmaceutical composition comprising the compound of the present invention as an active ingredient may be usefully used for the prevention or treatment of a cancer, multiple sclerosis (MS), a cardiovascular disease, central nervous system injury and an inflammatory disease. The cancer may be selected from a group consisting of a cancer of head, neck, eyes, mouth, throat, esophagus, bronchus, larynx, pharynx, chest, bone, lungs, colon, rectum, stomach, prostate, bladder, uterine, cervix, breast, ovaries, testices or other reproductive organs, skin, thyroid, blood, lymph nodes, kidneys, liver, pancreas, brain or central nervous system, a solid tumor, a blood-borne tumor, etc. Preferably, the tankyrase-related disease that can be prevented or treated using the pharmaceutical composition of the present invention may be colorectal cancer including colon cancer and rectal cancer, breast cancer, lung cancer or haematological malignancy, although not limited thereto.

The compound of the present invention may exist in the form of a pharmaceutically acceptable salt. An acid addition salt formed by a pharmaceutically acceptable free acid is useful as the salt. The term "pharmaceutically acceptable salt" used in the present invention refers to any organic or inorganic addition salt of the compound represented by Chemical Formula 1 which is at such a concentration that is relatively nontoxic to a patient and has a harmless effective action, and adverse side effects from the salt does not counteract benefits of the compound.

The acid addition salt may be prepared according to a commonly employed method, for example, by dissolving the compound in an excess amount of an aqueous acid solution and precipitating the salt using a water-miscible organic solvent, e.g., methanol, ethanol, acetone or acetonitrile. After heating the compound with an equimolar acid or alcohol (e.g., glycol monomethyl ether) in water, the mixture may be dried via evaporation, or the precipitated salt may be filtered through suction.

Here, a free acid may be an organic acid or an inorganic acid. As an inorganic acid, hydrochloric acid, phosphoric acid, sulfuric acid, nitric acid, stannic acid, etc. may be used and, as an organic acid, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic and, ascorbic acid, carbonic acid, vanillic acid, hydroiodic acid, etc. may be used, although not limited thereto.

Furthermore, a pharmaceutically acceptable metal salt may be prepared using a base. An alkali metal salt or an alkaline earth metal salt may be obtained, for example, by dissolving the compound in an excess amount of an alkali metal hydroxide or alkaline earth metal hydroxide solution, filtering an undissolved compound salt and then evaporating and drying the filtrate. Preparably, as the metal salt, a sodium, potassium or calcium salt may be pharmaceutically suitable, although not limited thereto. Also, a corresponding silver salt may be obtained by reacting the alkali metal or alkaline earth metal salt with an appropriate silver salt (e.g., silver nitrate).

Unless specified otherwise, the pharmaceutically acceptable salt of the compound of the present invention includes a plausible acidic or basic salt of the compound of Chemical Formula 1. For example, the pharmaceutically acceptable salt includes sodium, calcium and potassium salts having a hydroxyl group. In addition, hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts having an amino group may be included as other pharmaceutically acceptable salts. They may be prepared by salt preparation methods known in the art.

The pharmaceutically acceptable salt of imidazotriazinone or imidazopyrazinone derivative of the present invention may be any pharmaceutically acceptable salt of imidazotriazinone or imidazopyrazinone derivatives which exhibit inhibitory activity against tankyrase 1 and/or tankyrase 2, which is equivalent to that of imidazotriazinone or imidazopyrazinone derivative compounds, without limitation.

In the present invention, the term "prevention" refers to any act of inhibiting or retarding the onset, development and recurrence of tankyrase-related diseases by administering the composition of the present invention, and the term "treatment" refers to any act of ameliorating or improving symptoms of the diseases by administering the composition of the present invention.

Since the composition of the present invention can prevent or treat tankyrase-related disease by inhibiting the activity of tankyrase 1 and/or tankyrase 2 and thereby regulating cell death proliferation and/or metastasis, it can be usefully used to prevent or treat a diseased induced by abnormal activity of tankyrase 1 and/or tankyrase 2.

Preferably, the pharmaceutical composition according to the present invention may contain 0.1 wt % to 75 wt %, more preferably 1 wt % to 50 wt %, of the compound represented by Chemical Formula 1, the tautomer thereof, the stereoisomer thereof and their mixture or the pharmaceutically acceptable salt thereof as an active ingredient, based on the total weight of the composition.

The composition of the present invention may further contain a pharmaceutically acceptable carrier, diluent, or excipient, and may be prepared into various formulations including oral formulations such as powder, granule, tablet, capsule, suspension, emulsion, syrup, aerosol, etc., sterile injection solution, etc. according to commonly employed methods. It may be administered orally or via various routes including intravenous, intraperitoneal, subcutaneous, rectal and topical routes. Examples of the suitable carrier, excipient, or diluent that can be contained in the composition may include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. In addition, the composition of the present invention may further contain a filler, an anti-aggregant, a lubricant, a wetting agent, a fragrance, an emulsifier, a preservative, etc.

Solid formulations for oral administration may include tablet, pill, powder, granule, capsule, etc. These solid formulations may be prepared by mixing at least one excipient, e.g., starch, calcium carbonate, sucrose, lactose, gelatin, etc., in the composition. In addition to a simple excipient, a lubricant such as magnesium stearate and talc may be used.

Liquid formulations for oral administration may be exemplified by suspension, solution for internal application, emulsion, syrup, etc. In addition to a commonly used simple diluent such as water and liquid paraffin, various excipients such as a wetting agent, a sweetener, an aromatic, a preservative, etc. may be included.

Formulations for parenteral administration may include sterilized aqueous solution, non-aqueous solution, suspension, emulsion, lyophilizate and suppository. For the non-aqueous solution or suspension, propylene glycol, polyethylene glycol, vegetable oil such as olive oil, injectable ester such as ethyl oleate, etc. may be used. As a base for the suppository, witepsol, macrogol, tween 61, cacao butter, laurin butter, glycerogelatin, etc. may be used. Meanwhile, injectable formulations may contain commonly used additives such as a solubilizer, an isotonizing agent, a suspending agent, an emulsifier, a stabilizer, a preservative, etc.

The composition of the present invention is administered in a pharmaceutically effective amount. In the present invention, the term "pharmaceutically effective amount" refers to an amount which is sufficient to treat a disease at a reasonable benefit/risk ratio applicable for medical treatment without causing side effects. The level of effective dosage may be determined based on the health condition of a patient, a kind of disease and severity thereof, drug activity, sensitivity to the drug, administration method, administration time, administration route, rate of excretion, treatment period, drugs used in combination or simultaneously and other factors well known in the medical field. The composition of the present invention may be administered as an independent therapeutic agent or in combination with other therapeutic agent(s) sequentially or simultaneously. Also, it may be administered in the form of a single dose or multidoses. It is important to administer an amount that can derive the maximum effects with the minimum amount with no side effect in consideration of all the above-described factors, which can be easily determined by those skilled in the art.

Specifically, the effective amount of the compound in the composition of the present invention may vary depending on the age, sex and body weight of a patient. In general, an amount of 1 mg to 100 mg, preferably 5 mg to 60 mg, per kg body weight may be administered once a day, once in two days or 1 to 3 times a day. However, since the administration dosage can be increased or decreased depending on the administration route, severity of disease, sex, body weight, and age, etc., it does not limit the scope of the present invention by any means.

The present invention also provides a method for preventing or treating a tankyrase-related disease of a subject, which includes administering the compound represented by Chemical Formula 1, the tautomer thereof, the stereoisomer thereof and their mixture or the pharmaceutically acceptable salt thereof to the subject in need thereof.

In the present invention, the term "subject" refers to an animal in which a tankyrase-related disease has occurred or is likely to occur, including human, monkey, cow, horse, sheep, pig, chicken, turkey, quail, cat, dog, mouse, rat, rabbit or guinea pig. The disease may be effectively prevented or treated by administering the pharmaceutical composition of the present invention to the subject. The pharmaceutical composition of the present invention may be administered in combination with existing therapeutic agent.

In the present invention, the term "administration" refers to introduction of a desired substance to a patient in any appropriate way. The composition of the present invention may be administered via any general administration route as long as it can reach a target tissue. For example, the composition may be administered intraperitoneally, intravenously, intramuscularly, subcutaneously, intradermally, orally, topically, intranasally, intrapulmonarily or rectally, although not limited thereto. In addition, the pharmaceutical composition of the present invention may be administered by any apparatus that can deliver an active substance to a target cell. Preferred administration methods and formulations include intravenous injection, subcutaneous injection, intradermal injection, intramuscular injection, bolus injection, etc. The injection may be prepared using water-based solutions such as physiological saline, Ringer's solution, etc., or non-water-based solutions such as vegetable oils, higher fatty acid esters (e.g., ethyl oleate), alcohols (e.g., ethanol, benzyl alcohol, propylene glycol, glycerin, etc.), and may contain a pharmaceutical excipient such as a stabilizer for preventing denaturation (e.g., ascorbic acid, sodium bisulfife, sodium pyrosulfite, BHA, tocopherol, EDTA, etc.), an emulsifier, a buffer for pH control, a preservative for inhibiting microbial growth (e.g., phenylmercuric nitrate, thimerosal, benzalkonium chloride, phenol, cresol, benzyl alcohol, etc.), etc.

In the present invention, the term "therapeutically effective amount" used in combination with an active ingredient refers to an amount of the imidazotriazinone or imidazopyrazinone derivative compound, the tautomer thereof, the stereoisomer thereof and their mixture or the pharmaceutically acceptable salt thereof which is effective in preventing or treating a target disease.

In addition to the imidazotriazinone or imidazopyrazinone derivative compound, the tautomer thereof, the stereoisomer thereof and their mixture or the pharmaceutically acceptable salt thereof as the active ingredient, the pharmaceutical composition of the present invention may further comprise a drug used and known for the prevention or treatment of a particular disease depending on a kind of a disease to be prevented or treated. For example, when used for prevention or treatment of a cancer, the composition may further contain, in addition to the imidazotriazinone or imidazopyrazinone derivative compound, the tautomer thereof, the stereoisomer thereof and their mixture or the pharmaceutically acceptable salt thereof as the active ingredient, a known anti-cancer agent. Also, other therapies may be used in combination to treat the disease, which include chemotherapy, radiation therapy, hormone therapy, bone marrow transplantation, stem cell replacement therapy, other biological therapies, immunotherapy, etc., although not limited thereto.

Examples of anti-cancer agents that can be contained in the pharmaceutical composition of the present invention include a DNA alkylating agent such as mechlorethamine, chlorambucil, phenylalanine, mustard, cyclophosphamide, ifosfamide, carmustine (BCNU), lomustine (CCNU), streptozotocin, busulfan, thiotepa, cisplatin and carboplatin; an anti-cancer antibiotic such as dactinomycin (actinomycin D), doxorubicin (Adriamycin), daunorubicin, idarubicin, mitoxantrone, plicamycin, mitomycin C and bleomycin; and a plant alkaloid such as vincristine, vinblastine, paclitaxel, docetaxel, etoposide, teniposide, topotecan and iridotecan, etc., although not limited thereto.

Advantageous Effects of Invention

Since a novel imidazotriazinone or imidazopyrazinone derivative of the present invention can inhibit tankyrase 1 and/or tankyrase 2, it can be effectively used to treat or prevent a disease induced by overexpression or hyperactivation of tankyrases.

BEST MODE FOR CARRYING OUT THE INVENTION

Hereinafter, the constitution and effect of the present invention will be described in more detail through Examples. However, the following Examples are for illustrative purposes only and the scope of the present invention is not limited by the examples.

Preparation Example 1: 2-Chloro-7-methylimidazo [1,5-f][1,2,4]triazin-4(3H)-one (I-6)

2-Chloro-7-methylimidazo[1,5-f][1,2,4]triazin-4(3H)-one (I-6) was prepared as an intermediate for derivatives of triazolopyrimidinone based on the following reaction scheme.

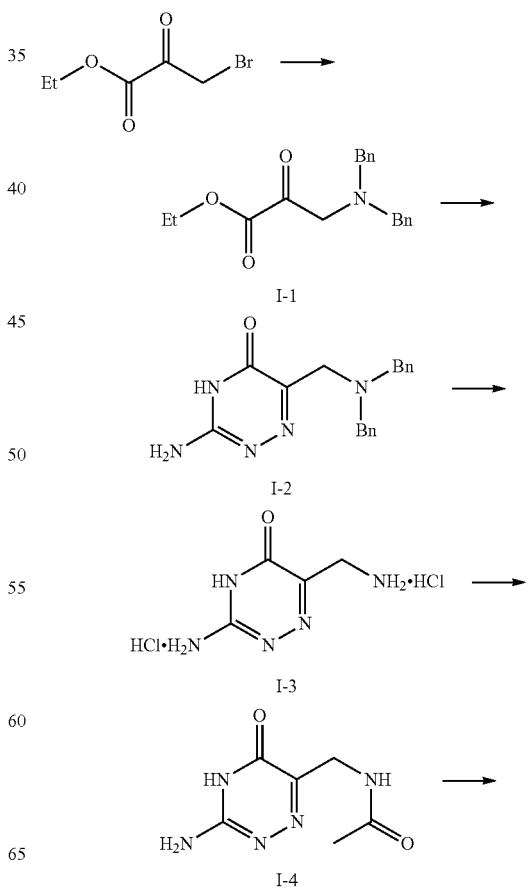

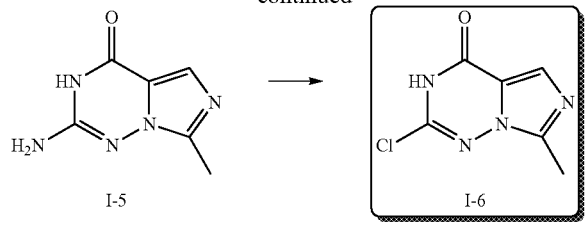

1.1. Ethyl 3-(dibenzylamino)-2-oxopropanoate

A mixture of bromopyruvate (100 mmol) and dibenzylamine (2 equiv) in butanone was heated to reflux for 1 h to synthesize ethyl 3-(dibenzylamino)-2-oxopropanoate (I-1, 40.254 mmol).

1.2. 3-Amino-6-((dibenzylamino)methyl)-1,2,4-triazin-5(4H)-one

A mixture of the intermediate I-1 and aminoguanidine bicarbonate (1.1 equiv) in EtOH was heated to reflux for 16 h to afford 3-amino-6-((dibenzylamino)methyl)-1,2,4-triazin-5(4H)-one (I-2; yield 68%).

1.3. 3-Amino-6-(aminomethyl)-1,2,4-triazin-5(4H)-one dihydrochloride

The intermediate I-2 was hydrogenated at rt for 48 h in 2 N HCl in EtOH using Pd/C (20 wt %) catalyst to afford 3-amino-6-(aminomethyl)-1,2,4-triazin-5(4H)-one dihydrochloride (I-3; yield 98%).

1.4. N-((3-Amino-5-oxo-4,5-dihydro-1,2,4-triazin-6-yl)methyl)acetamide

The intermediate I-3 was reacted with acetic anhydride (2 equiv) and sodium bicarbonate (3 equiv) in a 1:1:1 mixture of THF/MeCN/H2O at rt for 7 h to afford N-((3-amino-5-oxo-4,5-dihydro-1,2,4-triazin-6-yl)methyl)acetamide (I-4; yield 71%).

1.5. 2-Amino-7-methylimidazo[1,5-f][1,2,4]triazin-4(3H)-one

The intermediate I-4 was cyclized by heating to reflux with POCl$_3$ (10 equiv) in 1,2-dichloroethane for 8 h to afford 2-amino-7-methylimidazo[1,5-f][1,2,4]triazin-4(3H)-one (I-5; yield 77%).

1.6. 2-Chloro-7-methylimidazo[1,5-f][1,2,4]triazin-4(3H)-one (I-6)

The intermediate I-5 was reacted with tert-butyl nitrite (7 equiv) and antimony trichloride (2 equiv) in 1,2-dichloroethane at rt for 18 h to afford 2-chloro-7-methylimidazo[1,5-f][1,2,4]triazin-4(3H)-one (I-6; yield 43%).

LC-MS (ESI, m/z)=184.9 (M$^+$+1).

Preparation Example 2: 1-(2,6-difluoro-4-substituted-phenyl)piperazine hydrochloride (I-2A through I-2E), 4-(2-(3,5-difluoro-4-(piperazin-1-yl)phenoxy)ethyl)morpholine hydrochloride (I-2F) and 2-(3,5-difluoro-4-(piperazin-1-yl)phenoxy)-N,N-dimethylethan-1-amine hydrochloride (I-2G)

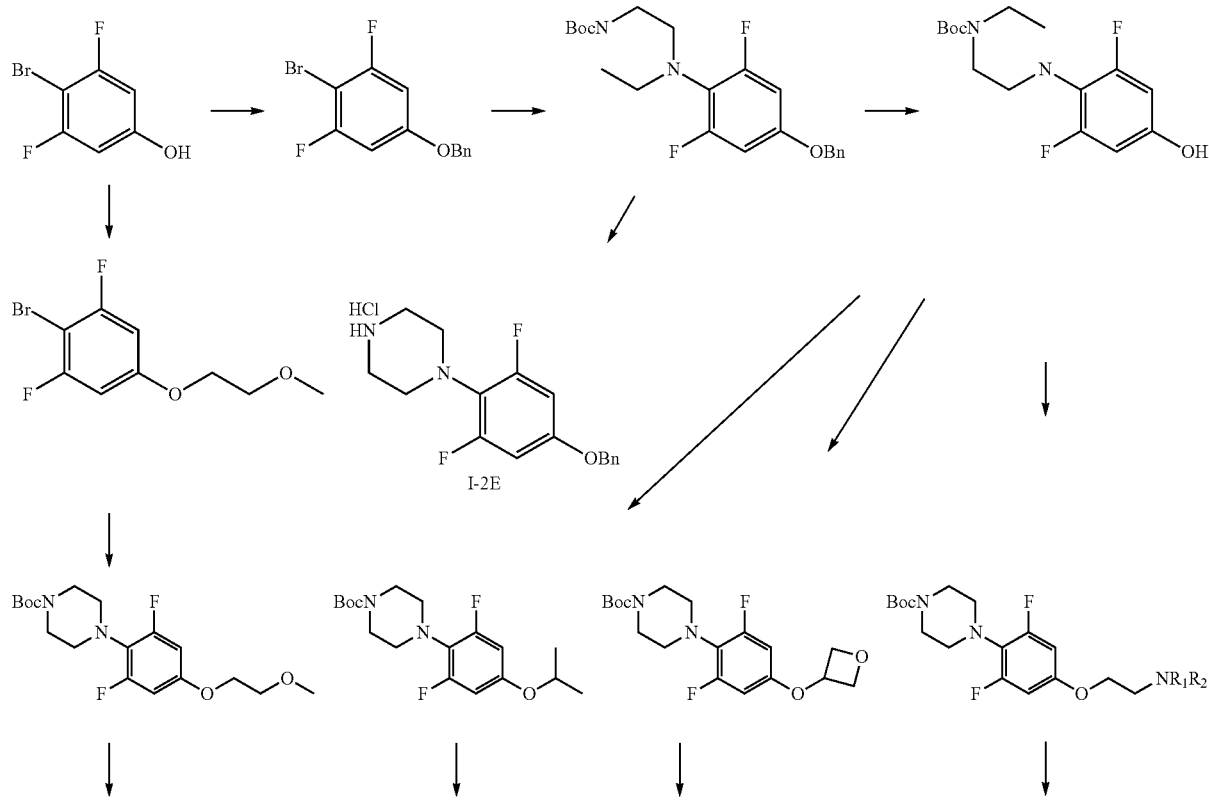

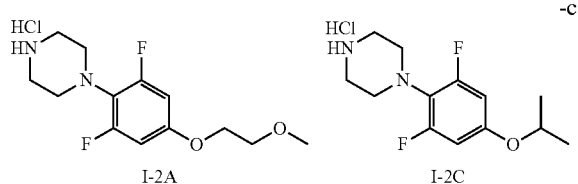
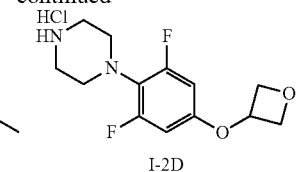
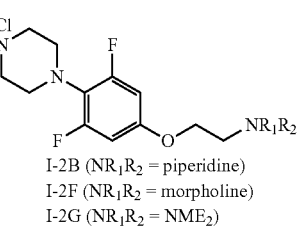

I-2A    I-2C    I-2D    I-2B (NR₁R₂ = piperidine)
                        I-2F (NR₁R₂ = morpholine)
                        I-2G (NR₁R₂ = NME₂)

2.1. Preparation of 5-(benzyloxy)-2-bromo-1,3-difluorobenzene

A mixture of 4-bromo-3,5-difluorophenol (7 g, 33.49 mmol), benzyl bromide (4.0 mL, 40.18 mmol) and $K_2CO_3$ (13.8 g, 100.47 mmol) in DMF (83 mL) was heated under microwave heating condition at 90° C. for 14 h. After cooling down to rt, the reaction mixture was diluted with EtOAc and washed with water. The organic layer was dried over $Na_2SO_4$, and concentrated under reduced pressure to afford the desired product (9.6 g) as a yellow oil.

LC-MS (ESI, m/z)=299.0 (M+H⁺).

2.2. tert-Butyl 4-(4-(benzyloxy)-2,6-difluorophenyl)piperazine-1-carboxylate A mixture of the compound (1 g, 3.34 mmol) obtained in Preparation Example 2.1, Boc-piperazine (1.49 g, 8.02 mmol), sodium tert-butoxide (898 mg, 9.352 mmol), BINAP (249 mg, 0.4 mmol) and $Pd_2(dba)_3$ (122 mg, 0.133 mmol), in toluene (10 mL) was heated under microwave heating condition at 130° C. for 20 min. After cooling down to rt, the mixture was concentrated under reduced pressure and purified by column chromatography to afford the desired product (459 mg) as a pink solid.

LC-MS (ESI, m/z)=405.2 (M⁺).

2.3. tert-Butyl 4-(2,6-difluoro-4-hydroxyphenyl)piperazine-1-carboxylate

To a solution of the compound (200 mg, 0.917 mmol) obtained in Preparation Example 2.2 in MeOH (2.5 mL) was added 10% Pd/C. After stirring at rt for 3 h under hydrogen gas, the reaction mixture was filtered through a Celite pad. The filtrate was concentrated under reduced pressure to afford the desired product (154 mg, 0.489 mmol, 98%) as a white solid.

2.4. tert-Butyl 4-(2,6-difluoro-4-(2-(piperidin-1-yl)ethoxy)phenyl)piperazine-1-carboxylate A mixture of the phenolic compound (300 mg, 0.954 mmol), 1-(2-chloroethyl)piperidine hydrochloride (211 mg, 1.145 mmol), and $K_2CO_3$ (527 mg, 3.816 mmol) in DMF (3.0 mL) was heated to 50° C. to 60° C. for 17 h. After cooling down to rt, the mixture was diluted with EtOAc and washed with water. The organic layer was dried over $Na_2SO_4$ and concentrated under reduced pressure to afford the desired product (390 mg) as a white solid.

LC-MS (ESI, m/z)=426.2 (M+H⁺).

2.5. 1-(2,6-Difluoro-4-(2-(piperidin-1-yl)ethoxy)phenyl)piperazine dihydrochloride To a solution of the compound (390 mg, 0.917 mmol) obtained in Preparation Example 2.4 in $CH_2Cl_2$ (1 mL) and MeOH (0.5 mL) was added 4 M HCl (3 mL). After stirring at rt for 4 h, the reaction mixture was concentrated under reduced pressure to afford the desired product I-2B (390 mg) as a white solid LC-MS (ESI, m/z)=326.2 (M⁺).

2.6. 1-(2,6-Difluoro-4-(2-(methoxyethoxy)phenyl)piperazine hydrochloride

The compound I-2A was prepared by the following sequence of reactions: O-alkylation used in Preparation Example 3.1, N-arylation used in Preparation Example 2.2, and Boc-group deprotection used in Preparation Example 2.5.

LC-MS (ESI, m/z)=272.2 (M⁺).

In an analogous manner the following compounds synthesized following the above procedure (Preparation Example 3.4 and 3.5):

2.7. 1-(2,6-Difluoro-4-isopropoxyphenyl)piperazine hydrochloride

From tert-butyl 4-(2,6-difluoro-4-hydroxyphenyl)piperazine-1-carboxylate and 2-iodopropane, 1-(2,6-difluoro-4-isopropoxyphenyl)piperazine hydrochloride was obtained (I-2C).

LC-MS (ESI, m/z)=257.3 (M+H⁺).

2.8. 1-(2,6-Difluoro-4-(oxetan-3-yloxy)phenyl)piperazine hydrochloride

From tert-butyl 4-(2,6-difluoro-4-hydroxyphenyl)piperazine-1-carboxylate and oxetan-3-yl 4-methylbenzenesulfonate, 1-(2,6-difluoro-4-(oxetan-3-yloxy)phenyl)piperazine hydrochloride was obtained (I-2D).

LC-MS (ESI, m/z)=271.3 (M+H⁺)

2.9. 1-(4-(Benzyloxy)-2,6-difluorophenyl)piperazine hydrochloride

From tert-butyl 4-(2,6-difluoro-4-hydroxyphenyl)piperazine-1-carboxylate and (bromomethyl)benzene, 1-(4-(benzyloxy)-2,6-difluorophenyl)piperazine hydrochloride was obtained (I-2E).

LC-MS (ESI, m/z)=305.3 (M+H⁺).

2.10. 4-(2-(3,5-Difluoro-4-(piperazin-1-yl)phenoxy)ethyl)morpholine dihydrochloride From tert-butyl 4-(2,6-difluoro-4-hydroxyphenyl)piperazine-1-carboxylate and 4-(2-chloroethyl)morpholine hydrochloride, 4-(2-(3,5-difluoro-4-(piperazin-1-yl)phenoxy)ethyl)morpholine dihydrochloride was obtained (I-2F).

LC-MS (ESI, m/z)=328.4 (M+H⁺).

2.11. 2-(3,5-Difluoro-4-(piperazin-1-yl)phenoxy)-N, N-dimethylethan-1-amine dihydrochloride From tert-butyl 4-(2,6-difluoro-4-hydroxyphenyl)piperazine-1-carboxylate and 2-chloro-N,N-dimethylethanamine hydrochloride, 2-(3,5-difluoro-4-(piperazin-1-yl)phenoxy)-N,N-dimethylethan-1-amine dihydrochloride was obtained (I-2G).
LC-MS (ESI, m/z)=286.3 (M+H$^+$).

Preparation Example 3: 4-(3,5-Difluoro-4-(piperazin-1-yl)benzyl)morpholine dihydrochloride

3.1. tert-Butyl 4-(2,6-difluoro-4-formylphenyl)piperazine-1-carboxylate

A mixture of 3,4,5-trifluorobenzaldehyde (2 g, 12.493 mmol), Boc-piperazine (2.33 g, 12.493 mmol), and K$_2$CO$_3$ (3.45 g, 24.986 mmol) in DMF (4 mL) was heated to 110° C. to 120° C. for 18 h. After cooling down to rt, the mixture was diluted with EtOAc and washed with water. The organic layer was dried over Na$_2$SO$_4$ and concentrated under reduced pressure. The residue was purified by column chromatography to afford the desired product (2.7 g) as a yellow solid.
LC-MS (ESI, m/z)=327.1 (M$^+$).

3.2. tert-Butyl 4-(2,6-difluoro-4-(morpholinomethyl)phenyl)piperazine-1-carboxylate A mixture of the compound (500 mg, 1.532 mmol) obtained in Preparation Example 3.1, morpholine (0.27 mL, 3.064 mmol), and Ti(i-Pro)$_4$ (0.91 mL, 3.064 mmol) in MeOH (5 mL) was stirred at rt for 17 h. NaCNBH$_3$ (193 mg, 3.064 mmol) was added to the reaction mixture at 0° C. and stirred at rt for 3 h. The mixture was concentrated under reduced pressure, and the residue was diluted with EtOAc and filtered through a Celite pad. The organic layer was washed with water, dried over Na$_2$SO$_4$, and concentrated under reduced pressure. The residue was purified by column chromatography to afford the desired product (272 mg) as a yellow oil.
LC-MS (ESI, m/z)=398.2 (M+H$^+$).

3.3. 4-(3,5-Difluoro-4-(piperazin-1-yl)benzyl)morpholine dihydrochloride

Using the compound obtained in Preparation Example 3.2, the desired product was prepared by following a similar method to that described in Preparation Example 2.5.
LC-MS (ESI, m/z)=298.1 (M+H$^+$).

Preparation Example 4: 1-(3,5-Difluoro-4-(piperazin-1-yl)phenyl)ethanol hydrochloride

4.1. tert-Butyl 4-(2,6-difluoro-4-(1-hydroxyethyl)phenyl)piperazine-1-carboxylate To a solution of the compound (600 mg, 1.839 mmol) obtained in Preparation Example 3.1, in THF (5 mL) was added dropwise 1.6 M MeLi in diethyl ether (1.26 mL, 2.023 mmol) at −78° C. for 2 h. The reaction mixture was slowly warmed to rt. After the reaction mixture was quenched with a few drops of water and concentrated under reduced pressure. The residue was diluted with EtOAc and washed with water. The organic layer was dried over Na$_2$SO$_4$ and concentrated under reduced pressure, and the residue was purified by column chromatography to afford the desired product (503 mg) as a yellow solid.
LC-MS (ESI, m/z)=342.2 (M+H$^+$).

4.2. 1-(3,5-Difluoro-4-(piperazin-1-yl)phenyl)ethanol hydrochloride

The compound (250 mg, 0.730 mmol) obtained in Preparation Example 4.1 was deprotected by 4 M HCl (4 mL) by following a similar method to that described in Preparation Example 3.5 to afford the desired product (226 mg, quant) as a yellow solid.
LC-MS (ESI, m/z)=243.1 (M+H$^+$).

Preparation Example 5: 1-(2,6-Difluoro-4-(1-methoxyethyl)phenyl)piperazine hydrochloride

5.1. tert-Butyl 4-(2,6-difluoro-4-(1-methoxyethyl)phenyl)piperazine-1-carboxylate To a solution of the compound (250 mg, 0.730 mmol) obtained in Preparation Example 4.1 in THF (2.5 mL) was added 55% NaH in mineral oil (53 mg, 1.095 nmmol) at 0° C. The reaction mixture was stirred for 10 min and dimethyl sulfate was added dropwise at 0° C. After stirring at rt for 1 h, the reaction mixture was concentrated under reduced pressure and diluted with EtOAc. The organic layer was washed with water, dried over Na$_2$SO$_4$, and concentrated under reduced pressure. The residue was purified by column chromatography to afford the desired product (294 mg) as a colorless oil.
LC-MS (ESI, m/z)=356.2 (M+H$^+$).

5.2. 1-(2,6-Difluoro-4-(1-methoxyethyl)phenyl)piperazine hydrochloride

Using the compound (294 mg, 0.730 mmol) obtained in Preparation Example 5.1, the compound (198 mg) was prepared by following a similar method to that described in Preparation Example 2.5.
LC-MS (ESI, m/z)=257.1 (M+H$^+$).

Preparation Example 6: 4-(2,6-Difluoro-4-(2-methoxyethoxy)phenyl)piperidin-4-ol hydrochloride

6.1. tert-Butyl 4-(2,6-difluoro-4-(2-methoxyethoxy)phenyl)piperazin-4-hydroxypiperidine-1-carboxylate To a solution of 2-bromo-1,3-difluoro-5-(2-methoxyethoxy)benzene (600 mg, 2.246 mmol) in ether (20 mL) was added dropwise 2.5 M n-BuLi in hexane (0.98 mL, 2.47 mmol) at −78° C. over 10 min. After stirring at −78° C. for 30 min and a solution of Boc-piperidone (537 mg, 2.69 mmol) in ether (4 mL) was added dropwise at −78° C. over 20 min. The reaction mixture was allowed to warm to rt for 1 h. After quenching with water (15 mL), and diluted with ether. The organic layer was dried over Na$_2$SO$_4$ and concentrated under reduced pressure to afford the desired product (1.01 g) as a yellow oil.
LC-MS (ESI, m/z)=388.2 (M+H$^+$).

6.2. 4-(2,6-Difluoro-4-(2-methoxyethoxy)phenyl)piperidin-4-ol hydrochloride

Using the desired product obtained in Preparation Example 6.1, the compound (370 mg) was prepared by following a similar method to that described in Preparation Example 2.5.
LC-MS (ESI, m/z)=288.1 (M+H$^+$).

23

Preparation Example 7:
4-(1H-Tetrazol-5-yl)piperidine hydrochloride

7.1. tert-Butyl 4-(1H-tetrazol-5-yl)piperidine-1-carboxylate

A mixture of tert-butyl 4-cyanopiperidine-1-carboxylate (1 g, 4.75 mmol), sodium azide (923 mg, 14.26 mmol), and ammonium chloride (763 g, 14.26 mmol) in DMF (9.4 mL) was heated to 140° C. for 20 h. After cooling down to rt, the reaction mixture diluted with EtOAc and washed with 0.5 N HCl and brine. The organic layer was dried over $Na_2SO_4$, and concentrated under reduced pressure. The solid was washed with ether and filtered to afford the desired product (764 mg).
LC-MS (ESI, m/z)=254.1 (M+H$^+$).

7.2. 4-(1H-Tetrazol-5-yl)piperidine hydrochloride

Using the compound obtained in Preparation Example 7.1, the compound was prepared by following a similar method to that described in Preparation Example 2.5.
LC-MS (ESI, m/z)=154.1 (M+H$^+$).

Preparation Examples 8 and 9: 3-(3,5-Difluoro-4-(piperazin-1-yl)phenyl)propane-1,2-diol hydrochloride (A) and 1-(3,5-difluoro-4-(piperazin-1-yl)phenyl)ethane-1,2-diol hydrochloride (B)

24

8.1. 1-(4-(2,6-Difluoro-4-nitrophenyl)piperazin-1-yl)ethan-1-one

A solution of 3,4,5-Trifluoronitrobenzene and N-acetylpiperazine in MeCN was heated to 60° C. for 1 h. The reaction mixture was concentrated under reduced pressure, and the residue was purified by column chromatography.
LC-MS (ESI, m/z)=287.2 (M+H$^+$).

8.2. 1-(4-(2,6-Difluoro-4-aminophenyl)piperazin-1-yl)ethan-1-one

The compound obtained in Preparation Example 8.1 was reduced by Pd/C hydrogenation. The residue was purified by column chromatography.
LC-MS (ESI, m/z)=256.2 (M+H$^+$).

8.3. 1-(4-(4-Bromo-2,6-difluorophenyl)piperazin-1-yl)ethan-1-one

The amine group of the compound obtained in Preparation Example 8.2 was replaced by bromide through the Sandmeyer reaction.
LC-MS (ESI, m/z)=319.0 (M+H$^+$).

8.4. 1-(4-(4-Allyl-2,6-difluorophenyl)piperazin-1-yl)ethan-1-one

An allyl group was introduced to the compound obtained in Preparation Example 8.3 by the Stille coupling reaction

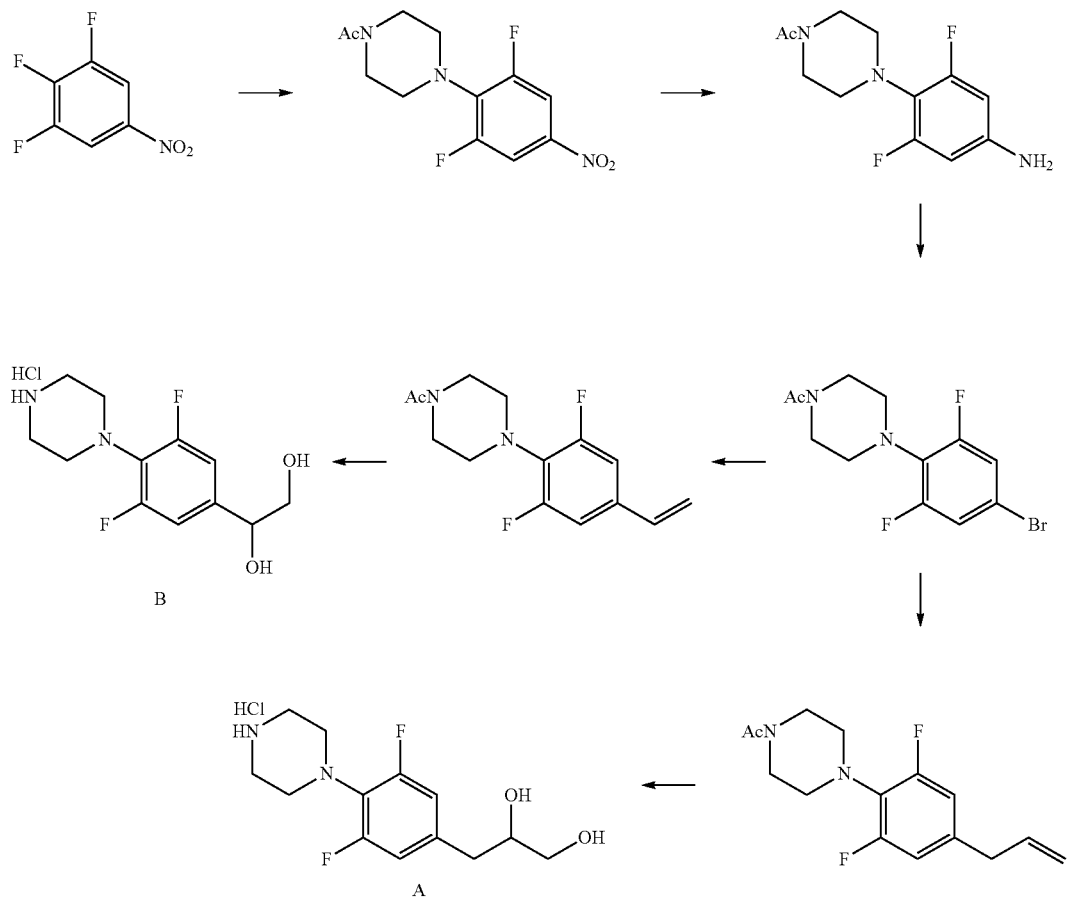

using Pd(PPh$_3$)$_4$, allylSnBu$_3$, and DMF (100° C., 18 h). Then, the desired product was purified by column chromatography.

LC-MS (ESI, m/z)=281.3 (M+H$^+$).

8.5. 3-(3,5-Difluoro-4-(piperazin-1-yl)phenyl)propane-1,2-diol hydrochloride (A)

The allylic compound obtained in Preparation Example 8.4 was dihydroxylated by OsO$_4$. Then, the desired product was afforded by removing the N-acetyl group under acidic conditions.

LC-MS (ESI, m/z)=273.3 (M$^+$).

9.1. 1-(4-(4-Vinyl-2,6-difluorophenyl)piperazin-1-yl)ethan-1-one

The vinyl group was introduced via the Stille coupling reaction employed in Preparation Example 8.3 using (vinyl)SnBu$_3$.

LC-MS (ESI, m/z)=267.3 (M+H$^+$).

9.2. 1-(3,5-Difluoro-4-(piperazin-1-yl)phenyl)ethane-1,2-diol hydrochloride (B)

The vinylic compound, obtained in Preparation Example 9.1, was dihydroxylated by OsO$_4$. Then, the compound B was obtained by removing the N-acetyl group of the dihydroxylated compound under acidic conditions.

LC-MS (ESI, m/z)=259.2 (M+H$^+$).

Preparation Example 10: 3,5-Difluoro-N-(2-methoxyethyl)-4-(piperazin-1-yl)aniline hydrochloride

10.1. tert-Butyl 4-(2,6-difluoro-4-nitrophenyl)piperazine-1-carboxylate

To a solution of 1,2,3-trifluoro-5-nitrobenzene (1 g, 5.65 mmol) in MeCN (11 mL) was added Boc-piperazine (2.63, 14.12 mmol) at rt. The reaction mixture was stirred at 60° C. for 3 h. After cooling down to rt, the mixture was diluted with EtOAc and washed with water. The organic layer was dried over Na$_2$SO$_4$ and concentrated under reduced pressure. The residue was purified by column chromatography to afford the desired product (1.93 g, quant) as a yellow solid.

LC-MS (ESI, m/z)=344.1 (M+H$^+$).

10.2. tert-Butyl 4-(4-amino-2,6-difluorophenyl)piperazine-1-carboxylate

The compound (1.75 g, 5.09 mmol) obtained in Preparation Example 10.1 was hydrogenated by Pd/C under hydrogen gas to afford the desired product (1.57 g) as a yellow solid.

LC-MS (ESI, m/z)=314.1 (M+H$^+$).

10.3. tert-Butyl 4-(2,6-difluoro-4-(2-methoxyethylamino)phenyl)piperazine-1-carboxylate To a solution of the compound (1.57 g, 5.01 mmol) obtained in Preparation Example 10.2 in DMF was added portionwise 55% NaH (437 mg, 10.02 mmol) at 0° C. over 30 min. A solution of 1-bromo-2-methoxyethane (835 mg, 6.01 mmol) in DMF (3 mL) was added dropwise to the reaction mixture at 0° C. After stirring overnight at rt the mixture was quenched with ice water and diluted with EtOAc. The organic layer was washed with water, dried over Na$_2$SO$_4$, and concentrated under reduced pressure. The residue was purified by column chromatography to afford the desired product (140 mg, quant) as a yellow oil.

LC-MS (ESI, m/z)=372.2 (M+H$^+$).

10.4. 3,5-Difluoro-N-(2-methoxyethyl)-4-(piperazin-1-yl)aniline hydrochloride The desired product (110 mg) was afforded as a white solid by deprotecting the compound (140 mg, 0.376 mmol) obtained in Preparation Example 10.3 using 4 M HCl.

LC-MS (ESI, m/z)=272.1 (M+H$^+$).

Preparation Example 11: 2-(3,5-Difluoro-4-(piperazin-1-yl)phenoxy)-1-(substituted-1-yl)ethanone hydrochloride (I-11A and I-11B), 1-(2,6-difluoro-4-(2-(pyrrolidin-1-yl)ethoxy)phenyl)piperazine hydrochloride (I-11C), 1-(2-(3,5-difluoro-4-(piperazin-4-yl)phenoxy)ethyl)-substituted hydrochloride (I-11D and I-11F), 1-(4-(2-azidoethoxy)-2,6-difluorophenyl)piperazine hydrochloride (I-11E) and benzyl 1-(2-(3,5-difluoro-4-(piperazin-1-yl)phenoxy)ethyl)piperidin-4-ylcarbamate hydrochloride (I-11G)

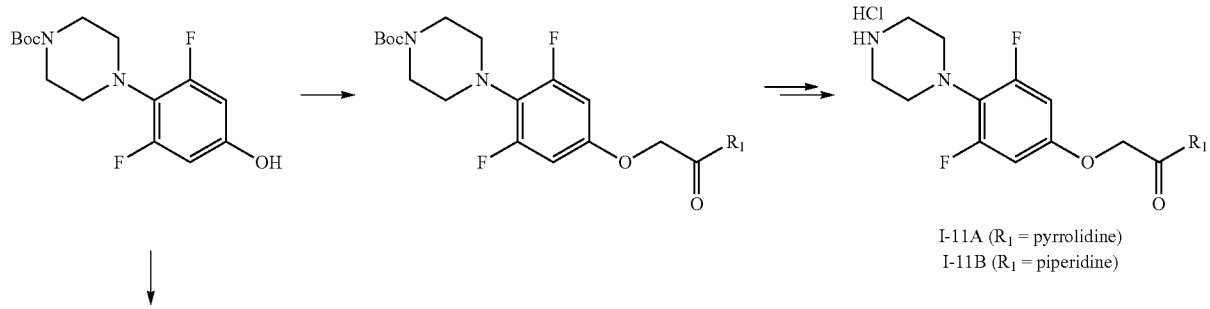

I-11A (R$_1$ = pyrrolidine)
I-11B (R$_1$ = piperidine)

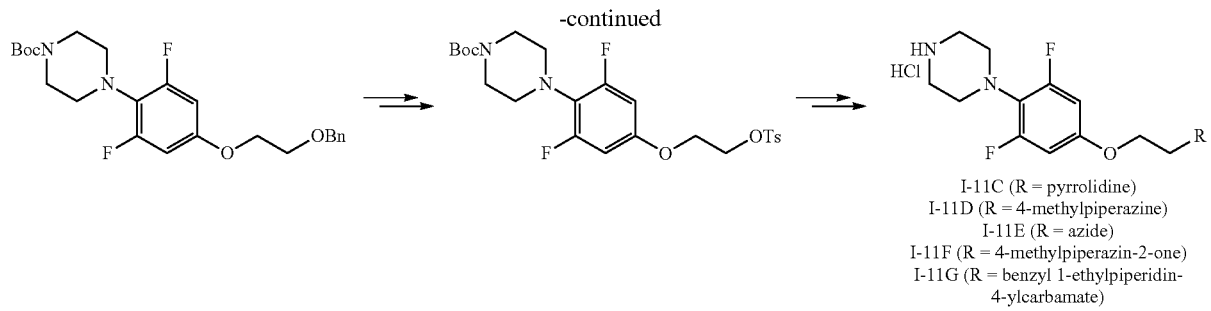

I-11C (R = pyrrolidine)
I-11D (R = 4-methylpiperazine)
I-11E (R = azide)
I-11F (R = 4-methylpiperazin-2-one)
I-11G (R = benzyl 1-ethylpiperidin-4-ylcarbamate)

11.1. tert-Butyl 4-(2,6-difluoro-4-(2-oxo-2-(pyrrolidin-1-yl)ethoxy)phenyl)piperazin-1-carboxylate To a solution of pyrrolidine (377.8 mg, 5.313 mmol) in THF (2.5 mL) was added dropwise a solution of 2-chloroacetyl chloride (300 mg, 2.656 mmol) in THF (2.5 mL) at 0° C. over 5 min. After stirring at rt for additional 15 h, the reaction mixture was diluted with EtOAc and washed with water. The organic layer was dried over $Na_2SO_4$ and concentrated under reduced pressure to afford the desired product (438 mg) as a yellow oil. A mixture of 2-chloro-1-(pyrrolidin-1-yl)ethanone (169 mg, 1.145 mmol), the compound (300 mg, 0.954 mmol) obtained in Preparation Example 2.3, and $K_2CO_3$ (527 mg, 3.816 mmol) in DMF (3.2 mL) was stirred at rt for 17 h. The reaction mixture was diluted with EtOAc and washed with water. The organic layer was dried over $Na_2SO_4$ and concentrated under reduced pressure to afford the desired product (346 mg) as a white solid.

11.2. 2-(3,5-Difluoro-4-(piperazin-1-yl)phenoxy)-1-(pyrrolidin-1-yl)ethanone hydrochloride (I-11A)

To a solution of tert-butyl 4-(2,6-difluoro-4-(2-oxo-2-(pyrrolidin-1-yl)ethoxy)phenyl)piperazin-1-carboxylate (336 mg, 0.790 mmol) in $CH_2Cl_2$ (0.5 mL) was added 4 M HCl (2 mL). The mixture was stirred at rt for 3 h, and concentrated under reduced pressure The residue was washed with ether to afford the desired product (295 mg) as a white solid.
LC-MS (ESI, m/z)=326.1 (M+H$^+$).

11.3. tert-Butyl 4-(2,6-difluoro-4-(2-oxo-2-(piperidin-1-yl)ethoxy)phenyl)piperazin-1-carboxylate The desired product was prepared in analogously with the procedure in Preparation Example 11.1.
LC-MS (ESI, m/z)=440.2 (M+H$^+$).

11.4. 2-(3,5-Difluoro-4-(piperazin-1-yl)phenoxy)-1-(piperidin-1-yl)ethanone hydrochloride (I-11B)

The compound (336 mg, 0.790 mmol), obtained in Preparation Example 11.3, was deprotected by 4 M HCl to afford the desired product (243 mg) as a white solid.
LC-MS (ESI, m/z)=340.1 (M+H$^+$).

11.5. tert-Butyl 4-(4-(2-(benzyloxy)ethoxy)-2,6-difluorophenyl)piperazin-1-carboxylate A mixture of the compound (1 g, 3.181 mmol) obtained in Preparation Example 2.3 benzyl-2-bromoethylamine (851 mg, 3.818 mmol) and $K_2CO_3$ (1.32 g, 9.544 mmol) in DMF (6.4 mL) was heated to 70° C. to 80° C. for 2 h. After cooling down to rt, the reaction mixture was diluted with EtOAc and washed with brine. The organic layer was dried over $Na_2SO_4$ and concentrated under reduced pressure to afford the desired product (1.427 g) as a yellow oil.
LC-MS (ESI, m/z)=449.2 (M+H$^+$).

11.6. tert-Butyl 4-(2,6-difluoro-4-(2-hydroxyethoxy)phenyl)piperazin-1-carboxylate To a solution of the compound (1.427 g, 3.181 mmol) obtained in Preparation Example 11.5 in MeOH (10.6 mL) was added 10% Pd/C (428 mg). After stirring at rt for 2 h under hydrogen gas, the mixture was filtered through a Celite pad. The filtrate was concentrated under reduced pressure to afford the desired product (1.14 g) as an apricot solid.
LC-MS (ESI, m/z)=359.1 (M+H$^+$).

11.7. tert-Butyl 4-(2,6-difluoro-4-(2-(tosyloxy)ethoxy)phenyl)piperazin-1-carboxylate A mixture of the compound (1.14 g, 3.181 mmol) obtained in Preparation Example 11.6, 4-methylbenzyl-1-sulfonyl chloride (909.8 mg, 4.722 mmol), TEA (504.8 mg, 7.953 mmol) and DMAP (97.2 mg, 0.057 mmol) in $CH_2Cl_2$ (10.6 mL) was stirred at rt for 3 h. The mixture was diluted with EtOAc and washed with 0.5 N HCl and saturated $NaHCO_3$. The organic layer was dried over $Na_2SO_4$, concentrated under reduced pressure to afford the desired product (1.44 g) as a white solid.
LC-MS (ESI, m/z)=513.2 (M+H$^+$).

11.8. tert-Butyl 4-(2,6-difluoro-4-(2-(4-methylpiperazin-1-yl)ethoxy)phenyl)piperazin-1-carboxylate To a solution of the compound (368 mg, 0.718 mmol) obtained in Preparation Example 11.7 and 1-methylpiperazine (143.8 mg, 1.436 mmol) in DMF (2.4 mL) was heated to 50° C. to 60° C. for 15 h. After cooling down to rt, the mixture was diluted with EtOAc and washed with water. The organic layer was dried over $Na_2SO_4$ and concentrated under reduced pressure to afford the desired product (270 mg) as a yellow oil.

11.9. 1-(2-(3,5-Difluoro-4-(piperazin-1-yl)phenoxy)ethyl)-4-methylpiperazine dihydrochloride (I-11D)

The compound (270 mg, 0.613 mmol) obtained in Preparation Example 11.8 was deprotected with 4 M HCl to afford the desired product (253 mg) as a white solid.
LC-MS (ESI, m/z)=341.2 (M+H$^+$).

11.10. 1-(2-(3,5-Difluoro-4-(piperazin-1-yl)phenoxy)ethyl)-4-pyrrolidine dihydrochloride (I-11C)

The desired product was synthesized by following reaction conditions similar to those used in Preparation Examples 11.8 and 11.9.
LC-MS (ESI, m/z)=312.2 (M+H$^+$).

11.11. 1-(4-(2-Azidoethoxy)-2,6-difluorophenyl)piperazine hydrochloride (I-11E)

The desired product was synthesized by following reaction conditions similar to those used in Preparation Examples 11.8 and 11.9.
LC-MS (ESI, m/z)=284.1 (M+H$^+$).

11.12. 1-(2-(3,5-Difluoro-4-(piperazin-1-yl)phenoxy)ethyl)-4-methylpiperazin-2-one hydrochloride (I-11F)

The desired product was synthesized by following reaction conditions similar to those used in Preparation Examples 11.8 and 11.9.
LC-MS (ESI, m/z)=355.2 (M+H$^+$).

11.13. Benzyl 1-(2-(3,5-difluoro-4-(piperazin-1-yl)phenoxy)ethyl)piperidin-4-ylcarbamate dihydrochloride (I-11G)

The desired product was synthesized by following reaction conditions similar to those used in Preparation Examples 11.8 and 11.9.
LC-MS (ESI, m/z)=475.2 (M+H$^+$).

Preparation Example 12: 1-(2-(3,5-difluoro-4-(piperazin-1-yl)phenoxy)ethyl)pyrrolidin-3-ol hydrochloride (I-12A) and 1-(2-(3,5-difluoro-4-(piperazin-1-yl)phenoxy)ethyl)piperidin-4-ol hydrochloride (I-12B)

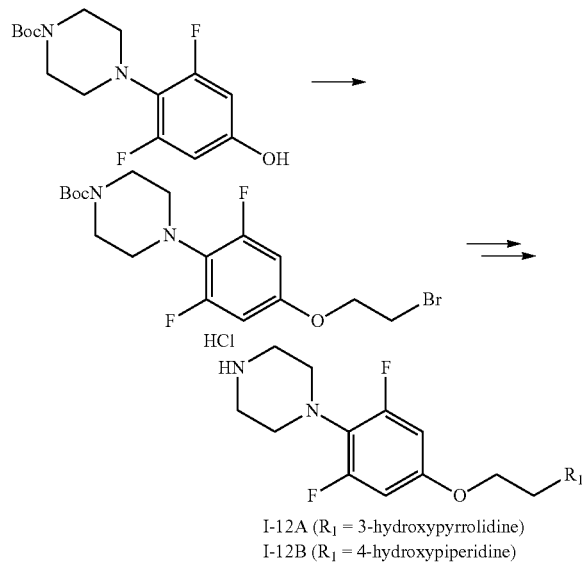

I-12A (R$_1$ = 3-hydroxypyrrolidine)
I-12B (R$_1$ = 4-hydroxypiperidine)

12.1. tert-Butyl 4-(4-(2-bromomethoxy)-2,6-difluorophenyl)piperazin-1-carboxylate A mixture of tert-butyl 4-(2,6-difluoro-4-hydroxyphenyl)piperazin-1-carboxylate (3.14 g, 10 mmol) and K$_2$CO$_3$ (4.2 g, 30 mmol) in MeCN (50 mL) was added 1,2-dibromoethane (3.8 g, 20 mmol). The reaction mixture was heated to reflux for 12 h. The reaction mixture was filtered and concentrated under reduced pressure. The residue was separated and purified by column chromatography to afford the desired product (3.5 g) as a white solid.

12.2. 1-(2-(3,5-Difluoro-4-(piperazin-1-yl)phenoxy)ethyl)pyrrolidin-3-ol hydrochloride (I-12A)

The aminated intermediate was prepared by reacting the compound (0.42 g, 1.00 mmol) obtained in Preparation Example 12.1 with Cs$_2$CO$_3$ (0.98 g, 3 mmol) and 3-hydroxypyrrolidine (0.13 g, 1.5 mmol) and in DMF (5 mL). The intermediate was treated with 4 M HCl to remove the Boc-group of piperidine to afford the desired product (0.3 g).

12.3. Preparation of 1-(2-(3,5-difluoro-4-(piperazin-1-yl)phenoxy)ethyl)piperidin-4-ol hydrochloride (I-12B)

The desired product was synthesized by a method similar to that used in Preparation Example 12.2.

Preparation Example 13: Preparation of 8-(benzyloxy)-6-chloro-3-methylimidazo[1,5-a]pyrazine (I-13)

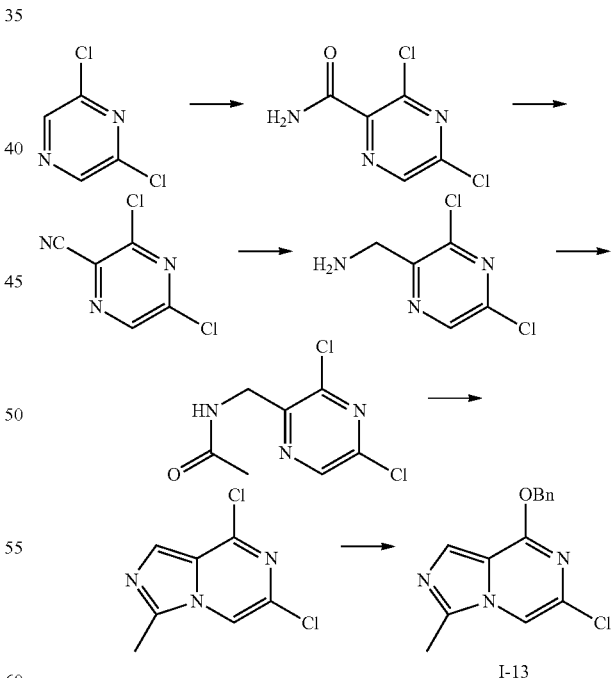

13.1. 3,5-Dichloropyrazin-2-carboxamide

To a mixture of 2,6-dichloropyrazine (11.0 g, 73.8 mmol) and formamide (58.6 mL, 1,476 mmol) was added dropwise sodium persulfate (17.1 g, 71.7 mmol). The reaction mixture was stirred at 90° C. for 2 h and was further stirred at rt for 12 h. After dilution with water, the mixture was extracted with isopropanol/chloroform (⅓) and washed with brine. The organic layer was dried over anhydrous magnesium sulfate, filtered, and concentrated under reduced pressure. The residue was purified by column chromatography (70% n-hexane/EtOAc) to afford 3,5-dichloropyrazin-2-carboxamide (5.06 g, 36%) as an oil.

$^1$H NMR (300 MHz, CDCl$_3$) δ=8.87 (s, 1H), 8.15 (s, 1H), 7.99 (s, 1H).

13.2. 3,5-Dichloropyrazin-2-carbonitrile

A solution of the compound (5.0 g, 13.3 mmol) obtained in Preparation Example 13.1 in MeCN (100 mL) was charged with POCl$_3$ (6.76 mL, 72.3 mmol) and stirred at 80° C. for 4 h. After dilution with water, the mixture was extracted with EtOAc and washed with brine. The organic layer was dried over anhydrous magnesium sulfate, filtered, and concentrated under reduced pressure. The crude product was purified by column chromatography (20% n-hexane/EtOAc) to afford 3,5-dichloropyrazin-2-carbonitrile (2.94 g, 65%) as a solid.

$^1$H NMR (300 MHz, CDCl3) δ=8.63 (s, 1H).

13.3. (3,5-Dichloropyrazin-2-yl)methanamine

The compound (3.40 g, 19.5 mmol) obtained in Preparation Example 13.2, acetic acid (70 mL), and Raney nickel (573 mg, 9.77 mmol) were added to an autoclave. After injection of hydrogen gas (~100 psi), the mixture was stirred at 50° C. for 24 h. The resulting mixture was filtered through a Celite pad. The solvent was evaporated, and the crude product was used in the next step without further purification.

13.4. N-((3,5-Dichloropyrazin-2-yl)methyl)acetamide

A mixture of the compound (3.40 g, 19.1 mmol) obtained in Preparation Example 13.3, anhydrous acetic acid (3.6 mL, 38.2 mmol), and triethylamine (10.6 mL, 76.4 mmol) in a MeCN (100 mL) and water (20 mL) was stirred at rt for 24 h. The resulting mixture was diluted with EtOAc and washed with saturated NaHCO$_3$. The organic layer was washed with brine, dried over anhydrous magnesium sulfate, filtered and concentrated under reduced pressure. The residue was purified by column chromatography (100% EtOAc) to afford N-((3,5-dichloropyrazin-2-yl)methyl)acetamide (3.46 g, 83%) as a white solid.

$^1$H NMR (300 MHz, CDCl3) δ=8.47 (s, 1H), 6.62 (brs, 1H), 4.66 (d, J=4.7 Hz, 2H), 2.01 (s, 3H).

13.5. 6,8-Dichloro-3-methylimidazo[1,5-a]pyrazine

To a solution of the compound (2.50 g, 11.4 mmol) obtained in Preparation Example 13.4 in MeCN (150 mL) and DMF (5 mL), POCl$_3$ (1.28 mL, 13.7 mmol) was added dropwise and the mixture was stirred at 70° C. for 24 h. Upon completion of the reaction, the mixture was diluted with EtOAc and washed with saturated NaHCO$_3$. The organic layer was washed with brine, dried over anhydrous magnesium sulfate, filtered and concentrated under reduced pressure. The crude product was purified by column chromatography (100% EtOAc) to afford 6,8-dichloro-3-methylimidazo[1,5-a]pyrazine (2.24 g, 97%) as a yellow solid.

$^1$H NMR (300 MHz, CDCl3) δ=7.83 (s, 1H), 7.64 (s, 1H), 2.67 (s, 3H).

13.6. 8-(Benzyloxy)-6-chloro-3-methylimidazo[1,5-a]pyrazine (I-13)

To a solution of NaH (161 mg, 4.03 mmol) and benzylalcohol (0.42 mL, 4.03 mmol) in THF (10 mL), the compound obtained in Preparation Example 13.5 (740 mg, 3.66 mmol) was added dropwise after 20 min, and the mixture was stirred at rt for 2 h. The reaction mixture was diluted with water and extracted with EtOAc. The resulting product was washed with brine, dried over anhydrous magnesium sulfate, filtered and concentrated under reduced pressure. The crude product was purified by column chromatography (80% n-hexane/EtOAc) to afford the desired product I-13 (588 mg, 59%) as a solid.

$^1$H NMR (300 MHz, CDCl3) δ=7.86 (m, 1H), 7.47 (m, 2H), 7.36 (m, 4H), 5.51 (s, 2H), 2.53 (s, 3H).

Example 1: 2-(4-(2-Fluorophenyl)piperazin-1-yl)-7-methylimidazo[1,5-f][1,2,4]triazin-4(3H)-one A mixture of 2-chloro-7-methylimidazo[1,5-f][1,2,4]triazin-4(3H)-one (intermediate I-6, 28 mg, 0.15 mmol), 1-(2-fluorophenyl)piperazine (54 mg, 0.3 mmol), and DIPEA (58 mg, 0.45 mmol) in EtOH (2 mL) was heated under microwave heating conditions at 150° C. for 30 min. The mixture was concentrated under reduced pressure and purified by column chromatography (20/1 CH$_2$Cl$_2$/MeOH) to afford the desired product.

LC-MS (ESI, m/z)=329.1 (M$^+$+1).

Example 2: 2-(4-(2,6-Difluoro-4-(2-methoxyethoxy)phenyl)piperazin-1-yl)-7-methylimidazo[1,5-f][1,2,4]triazin-4(3H)-one Following the general procedure of Example 1, the desired product was afforded using the amine (I-2A).

LC-MS (ESI, m/z)=420.6 (M$^+$).

Example 3: 2-(4-(4-(Benzyloxy)-2,6-difluorophenyl)piperazin-1-yl)-7-methylimidazo[1,5-f][1,2,4]triazin-4(3H)-one Following the general procedure of Example 1, the desired product was afforded using the amine (I-2E).

$^1$H NMR (300 MHz, CDCl3) δ=9.31 (s, 1H), 7.74 (s, 1H), 7.41-7.36 (m, 5H), 6.53 (d, J=9.0 Hz, 2H), 5.00 (s, 2H), 3.61 (bs, 4H), 3.25 (bs, 4H), 2.56 (s, 3H).

Example 4: 2-(4-(2,6-Difluoro-4-(2-morpholinoethoxy)phenyl)piperazin-1-yl)-7-methylimidazo[1,5-f][1,2,4]triazin-4(3H)-one Following the general procedure of Example 1, the desired product was afforded using the amine (I-2F).

LC-MS (ESI, m/z)=476.3 (M$^+$+1).

Example 5: 2-(4-(2,6-Difluoro-4-(2-(piperidin-1-yl)ethoxy)phenyl)piperazin-1-yl)-7-methylimidazo[1,5-f][1,2,4]triazin-4(3H)-one Following the general procedure of Example 1, the desired product was afforded using the amine (I-2B).

LC-MS (ESI, m/z)=474.3 (M$^+$+1).

Example 6: 2-(4-(4-(2-(Dimethylamino)ethoxy)-2,6-difluorophenyl)piperazin-1-yl)-7-methylimidazo[1,5-f][1,2,4]triazin-4(3H)-one Following the general procedure of Example 1, the desired product was afforded using the amine (I-2G).
LC-MS (ESI, m/z)=434.3 (M$^+$+1).

Example 7: 2-(4-(2,6-Difluoro-4-(2-hydroxyethoxy)phenyl)piperazin-1-yl)-7-methylimidazo[1,5-f][1,2,4]triazin-4(3H)-one Step 1: tert-Butyl 4-(2,6-difluoro-4-hydroxyphenyl)piperazine-1-carboxylate was alkylated using a method similar to that described in Preparation Example 2.3 to afford tert-butyl 4-(4-(2-benzyloxy-ethoxy)-2,6-difluoro-phenyl)-piperazine-1-carboxylate. The Boc-deprotected compound was obtained by treatment with HCl.
Step 2: A mixture of the amine (429 mg, 1.11 mmol) obtained in step 1, the intermediate I-6 (184 mg, 1.0 mmol), and DIPEA (174 mg, 1.35 mmol) in EtOH (3.0 mL) was heated under microwave heating conditions at 150° C. for 30 min. After cooling down to rt, the mixture was concentrated under reduced pressure and purified by CombiFlash Prep-MPLC (column, silica gel; mobile phase, increase from CH$_2$Cl$_2$:MeOH=99:1 to CH$_2$Cl$_2$:MeOH=85:15 over 18 min; detector, UV 254 nm) to afford 2-(4-(2,6-difluoro-4-(2-benzyloxyethoxy)phenyl)piperazin-1-yl)-7-methylimidazo[1,5-f][1,2,4]triazin-4(3H)-one.
Step 3: To a solution in CH$_2$Cl$_2$:MeOH (1 mL:1 mL) of 2-(4-(2,6-difluoro-4-(2-benzyloxyethoxy)phenyl)piperazin-1-yl)-7-methylimidazo[1,5-f][1,2,4]triazin-4(3H)-one (105 mg, 0.21 mmol) obtained in step 2, 10% Pd/C (40 mg) was added, and the reaction mixture was stirred at rt for 24 h under hydrogen gas. The mixture was filtered through a Celite pad and concentrated under reduced pressure. The resulting solid was recrystallized in MeOH/Et$_2$O to afford the desired product.
LC-MS (ESI, m/z)=407.2 (M$^+$+1).

Example 8: (S)-2-(3,5-Difluoro-4-(4-(7-methyl-4-oxo-3,4-dihydroimidazo[1,5-f][1,2,4]triazin-2-yl)piperazin-1-yl)phenoxy)ethyl 2-aminopropionate hydrochloride Step 1: A mixture of (S)-2-(tert-butoxycarbonylamino)propionic acid (24 mg, 0.129 mmol), the compound obtained in Example 7 (35 mg, 0.086 mmol), EDC-HCl (49 mg, 0.258 mmol), and HOBt (35 mg, 0.258 mmol) in CH$_2$Cl$_2$ (2 mL) was stirred at 25° C. for 17 h. The resulting mixture was concentrated under reduced pressure, and the residue was purified by column chromatography to afford the desired product (15 mg).
Step 2: To a solution in CH$_2$Cl$_2$ (2 mL) of the compound obtained in Step 1 (15 mg, 0.026 mmol), 4 M HCl in dioxane (104 μL) was added. The solution was stirred at 25° C. for 2 h. The resulting mixture was concentrated under reduced pressure to afford the desired product (13 mg).

Example 9: 2-(4-(4-(2,3-Dihydroxypropoxy)-2,6-difluorophenyl)piperazin-1-yl)-7-methylimidazo[1,5-f][1,2,4]triazin-4(3H)-one tert-Butyl 4-(2,6-difluoro-4-hydroxyphenyl)piperazin-1-carbonate was alkylated by treatment with glycidyl benzyl ether in MeCN in the presence of LiClO$_4$. After removal of the Boc protecting group, the amine thus produced was reacted with the intermediate I-6 to afford the corresponding coupling product, which was debenzylated to afford the desired product.
LC-MS (ESI, m/z)=437.2 (M$^+$+1).

Example 10: 2-(4-(2,6-Difluoro-4-(morpholinomethyl)phenyl)piperazin-1-yl)-7-methylimidazo[1,5-f][1,2,4]triazin-4(3H)-one Following the general procedure of Example 1, the desired product was afforded using the amine (4-(3,5-difluoro-4-(piperazin-1-yl)benzyl)morpholine dihydrochloride).
LC-MS (ESI, m/z)=446.3 (M$^+$+1).

Example 11: 2-(4-(2,6-Difluoro-4-((4-methylpiperazin-1-yl)methyl)phenyl)piperazin-1-yl)-7-methylimidazo[1,5-f][1,2,4]triazin-4(3H)-one Following the general procedure of Example 1, the desired product was afforded using the amine (1-((3,5-difluoro-4-(piperazin-1-yl)phenyl)methyl)-4-methylpiperazine dihydrochloride).
LC-MS (ESI, m/z)=459.4 (M$^+$+1).

Example 12: 2-(4-(2,6-Difluoro-4-(oxetan-3-yloxy)phenyl)piperazin-1-yl)-7-methylimidazo[1,5-f][1,2,4]triazin-4(3H)-one Following the general procedure of Example 1, the desired product was afforded using the amine (I-2D).
LC-MS (ESI, m/z)=419.3 (M$^+$+1).

Example 13: 2-(4-(2,6-Difluoro-4-(1-hydroxyethyl)phenyl)piperazin-1-yl)-7-methylimidazo[1,5-f][1,2,4]triazin-4(3H)-one Following the general procedure of Example 1, the desired product was afforded using the amine (4-(2,6-difluoro-4-(1-hydroxyethyl)-phenyl)-piperazine hydrochloride).
LC-MS (ESI, m/z)=391.3 (M$^+$+1).

Example 14: 2-(4-(2,6-Difluoro-4-(1-methoxyethyl)phenyl)piperazin-1-yl)-7-methylimidazo[1,5-f][1,2,4]triazin-4(3H)-one Following the general procedure of Example 1, the desired product was afforded using the amine (1-(2,6-difluoro-4-(1-methoxyethyl)phenyl)piperazine hydrochloride).
LC-MS (ESI, m/z)=405.2 (M$^+$+1).

Example 15: 2-(4-(2,6-Difluorophenyl)piperazin-1-yl)-7-methylimidazo[1,5-f][1,2,4]triazin-4(3H)-one Following the general procedure of Example 1, the desired product was afforded using the amine (1-(2,6-difluorophenyl)piperazine).
LC-MS (ESI, m/z)=347.2 (M$^+$+1).

Example 16: 2-(4-(2,4,6-Trifluorophenyl)piperazin-1-yl)-7-methylimidazo[1,5-f][1,2,4]triazin-4(3H)-one Following the general procedure of Example 1, the desired product was afforded using the amine (1-(2,4,6-trifluorophenyl)piperazine).
LC-MS (ESI, m/z)=365.2 (M$^+$+1).

Example 17: 2-(4-(2,6-Difluoro-4-(2-methoxy-ethoxy)phenyl)-4-hydroxypiperidin-1-yl)-7-methyl-imidazo[5,1-f][1,2,4]triazin-4(3H)-one Following the general procedure of Example 1, the desired product was afforded using the amine (4-(2,6-difluoro-4-(2-methoxyethoxy)phenyl)piperidin-4-ol).
LC-MS (ESI, m/z)=436.3 (M$^+$+1).

Example 18: 2-(4-(2,6-Difluoro-4-(2-methoxyethyl-amino)phenyl)piperazin-1-yl)-7-methylimidazo[5,1-f][1,2,4]triazin-4(3H)-one Following the general procedure of Example 1, the desired product was afforded using the amine (3,5-difluoro-N-(2-methoxyethyl)-4-(piperazin-1-yl)aniline hydrochloride).
LC-MS (ESI, m/z)=420.2 (M$^+$+1).

Example 19: 2-(4-(2,6-Difluoro-4-(((2-methoxy-ethyl)(methyl)amino)methyl)phenyl)piperazin-1-yl)-7-methylimidazo[1,5-f][1,2,4]triazin-4(3H)-one Following the general procedure of Example 1, the desired product was afforded using the amine (N-(3,5-difluoro-4-(piperazin-1-yl)benzyl)-2-methoxy-N-methyl-ethan-1-amine dihydrochloride).
LC-MS (ESI, m/z)=448.4 (M$^+$+1).

Example 20: 2-(4-(4-(1,2-Dihydroxyethyl)-2,6-difluorophenyl)piperazin-1-yl)-7-methylimidazo[1,5-f][1,2,4]triazin-4(3H)-one Following the general procedure of Example 1, the desired product was afforded using the amine (1-(3,5-difluoro-4-(piperazin-1-yl)phenyl)ethane-1,2-diol hydrochloride).
LC-MS (ESI, m/z)=407.2 (M$^+$+1).

Example 21: 2-(4-(4-(2,3-Dihydroxypropyl)-2,6-difluorophenyl)piperazin-1-yl)-7-methylimidazo[1,5-f][1,2,4]triazin-4(3H)-one Following the general procedure of Example 1, the desired product was afforded using the amine (3-(3,5-difluoro-4-(piperazin-1-yl)phenyl)propane-1,2-diol hydrochloride).
LC-MS (ESI, m/z)=420.3 (M$^+$+1).

Example 22: 2-(4-(1H-Tetrazol-5-yl)piperidin-1-yl)-7-methylimidazo[1,5-f][1,2,4]triazin-4(3H)-one Following the general procedure of Example 1, the desired product was afforded using the amine (4-(1H-tetrazol-5-yl)piperidine hydrochloride).
LC-MS (ESI, m/z)=302.2 (M$^+$+1).

Example 23: 7-Methyl-2-(4-(2-methyl-2H-tetrazol-5-yl)piperidin-1-yl)imidazo[1,5-f][1,2,4]triazin-4(3H)-one Following the general procedure of Example 1, the desired product was afforded using the amine (4-(2-methyl-2H-tetrazol-5-yl)piperidine hydrochloride).
LC-MS (ESI, m/z)=316.2 (M$^+$+1).

Example 24: 2-(4-(2,6-Difluoro-4-(2-(pyrrolidin-1-yl)ethoxy)phenyl)piperazin-1-yl)-7-methylimidazo[1,5-f][1,2,4]triazin-4(3H)-one Following the general procedure of Example 1, the desired product was afforded using the amine (I-11C).
LC-MS (ESI, m/z)=460.2 (M$^+$+1).

Example 25: 2-(4-(2,6-Difluoro-4-(2-(4-methylpip-erazin-1-yl)ethoxy)phenyl)piperazin-1-yl)-7-methyl-imidazo[1,5-f][1,2,4]triazin-4(3H)-one Following the general procedure of Example 1, the desired product was afforded using the amine (I-11D).
LC-MS (ESI, m/z)=489.2 (M$^+$+1).

Example 26: 2-(4-(2,6-Difluoro-4-(3-(piperidin-1-yl)propoxy)phenyl)piperazin-1-yl)-7-methylimidazo[1,5-f][1,2,4]triazin-4(3H)-one Following the general procedure of Example 1, the desired product was afforded using the amine (1-(2,6-difluoro-4-(3-(piperidin-1-yl)propoxy)phenyl)piperazine hydrochloride).
LC-MS (ESI, m/z)=488.2 (M$^+$+1).

Example 27: 2-(4-(4-(Bis(2-methoxyethyl)amino)-2,6-difluorophenyl)piperazin-1-yl)-7-methylimidazo[1,5-f][1,2,4]triazin-4(3H)-one Following the general procedure of Example 1, the desired product was afforded using the amine (3,5-difluoro-N,N-bis(2-methoxyethyl)-4-(piperazin-1-yl)aniline).
LC-MS (ESI, m/z)=478.2 (M$^+$+1).

Example 28: 2-(4-(2,6-Difluoro-4-(2-oxo-2-(piperidin-1-yl)ethoxy)phenyl)piperazin-1-yl)-7-methylimidazo[1,5-f][1,2,4]triazin-4(3H)-one Following the general procedure of Example 1, the desired product was afforded using the amine (I-11B).
LC-MS (ESI, m/z)=489.2 (M+H$^+$).

Example 29: 2-(4-(2,6-Difluoro-4-(2-oxo-2-(pyrrolidin-1-yl)ethoxy)phenyl)piperazin-1-yl)-7-methylimidazo[1,5-f][1,2,4]triazin-4(3H)-one Following the general procedure of Example 1, the desired product was afforded using the amine (I-11A).
LC-MS (ESI, m/z)=473.8 (M+H$^+$).

Example 30: 2-(4-(2,6-Difluoro-4-(2-piperidin-1-yl)ethoxy)-phenyl)-1,4-diazepan-1-yl)-7-methylimidazo[5,1-f][1,2,4]triazin-4(3H)-one Step 1: tert-Butyl 4-(4-(benzyloxy)-2,6-difluorophenyl)diazepan-1-carboxylate was afforded using a method similar to that described in Preparation Example 2.2, except by reaction with Boc-diazepane instead of Boc-piperazine.

Step 2: 4-(4-(Benzyloxy)-2,6-difluorophenyl)diazepane hydrochloride was afforded from the compound obtained in step 1 using a method similar to those described in Preparation Examples 2.3 to 2.6.

Step 3: The desired product was afforded by reacting the compound obtained in step 2 with the compound I-6, using a method similar to that described in Example 1.
LC-MS (ESI, m/z)=488.3 (M+H$^+$).

Example 31: 2-(4-(4-(2-Azidoethoxy)-2,6-difluorophenyl)piperazin-1-yl)-7-methylimidazo[1,5-f][1,2,4]triazin-4(3H)-one Following the general procedure of Example 1, the desired product was afforded using the amine (I-11E).
LC-MS (ESI, m/z)=431.7 (M+H$^+$).

Example 32: 2-(4-(4-(2-Aminoethoxy)-2,6-difluorophenyl)piperazin-1-yl)-7-methylimidazo[1,5-f][1,2,4]triazin-4(3H)-one To a solution in MeOH of the compound obtained in Example 31, 10% Pd/C was added, and the mixture was stirred under hydrogen gas for 2 h. The mixture was filtered through a Celite pad, concentrated under reduced pressure and washed with ether to afford the desired product.
LC-MS (ESI, m/z)=406.2 (M+H$^+$).

Example 33: 2-(4-(2,6-Difluoro-4-(2-(4-methyl-2-oxopiperazin-1-yl)ethoxy)phenyl)piperazin-1-yl)-7-methylimidazo[1,5-f][1,2,4]triazin-4(3H)-one Following the general procedure of Example 1, the desired product was afforded using the amine (I-11F).
LC-MS (ESI, m/z)=503.2 (M+H$^+$).

Example 34: 2-(4-(4-(2-(4-Aminopiperidin-1-yl)ethoxy)-2,6-difluorophenyl)piperazin-1-yl)-7-methylimidazo[1,5-f][1,2,4]triazin-4(3H)-one Step 1: Following the general procedure of Example 1, the Cbz-protected compound was afforded by the reaction of the compound I-6 with the amine (I-11G).
Step 2: Following the general procedure of Example 32, the desired product was afforded using the compound obtained in Step 1.
LC-MS (ESI, m/z)=489.2 (M+H$^+$).

Example 35: 2-(4-(2,6-Difluoro-4-(2-(3-hydroxypyrrolidin-1-yl)ethoxy)phenyl)piperazin-1-yl)-7-methylimidazo[1,5-f][1,2,4]triazin-4(3H)-one Following the general procedure of Example 1, the desired product was afforded using the amine (I-12A).
LC-MS (ESI, m/z)=476.0 (M+H$^+$).

Example 36: 2-(4-(2,6-Difluoro-4-(2-(4-hydroxypiperidin-1-yl)ethoxy)phenyl)piperazin-1-yl)-7-methylimidazo[1,5-f][1,2,4]triazin-4(3H)-one Following the general procedure of Example 1, the desired product was afforded using the amine (I-12B).
LC-MS (ESI, m/z)=490.1 (M+H$^+$).

Example 37: 6-(4-(2,6-Difluoro-4-(2-methoxyethoxy)phenyl)piperazin-1-yl)-3-methylimidazo[1,5-a]pyrazin-8(7H)-one Step 1: A mixture of the compound I-13 (195 mg, 0.710 mmol), the amine I-2A (195 mg, 0.852 mmol), sodium tert-butoxide (204.6 mg, 2.130 mmol), BINAP (44.2 mg, 0.035 mmol), and Pd$_2$(dba)$_3$ (32.5 mg, 0.133 mmol) in toluene was heated under microwave heating conditions at 150° C. for 20 min. After cooling down to rt, the resulting mixture was filtered through a Celite pad. The mixture was diluted with EtOAc and washed with water. The organic layer was dried over Na$_2$SO$_4$, filtered, and concentrated under reduced pressure. The residue was purified by column chromatography to afford the desired product.
Step 2: A solution in MeOH (0.68 mL) and EtOAc (0.2 mL) of the compound (104 mg, 0.204 mmol) obtained in step 1 was charged with 10% Pd/C (20 mg) and stirred under hydrogen gas for 24 h. The product was filtered through a Celite pad, and the filtrate was concentrated under reduced pressure and washed with ether to afford the desired product as a white solid.
LC-MS (ESI, m/z)=420.9 (M+H$^+$).

Example 38: 6-(4-(2,6-Difluoro-4-(2-morpholinoethoxy)phenyl)piperazin-1-yl)-3-methylimidazo[1,5-a]pyrazin-8(7H)-one Following the general procedure in Example 37, the desired product was afforded using the amine I-2F.
LC-MS (ESI, m/z)=475.0 (M+H$^+$).

Example 39: 6-(4-(2,6-Difluoro-4-(2-(piperidin-1-yl)ethoxy)phenyl)piperazin-1-yl)-3-methylimidazo[1,5-a]pyrazin-8(7H)-one Following the general procedure in Example 37, the desired product was afforded using the amine I-2B.
LC-MS (ESI, m/z)=473.1 (M+H$^+$).

Example 40: 6-(4-(4-(2-(Dimethylamino)ethoxy)-2,6-difluorophenyl)piperazin-1-yl)-3-methylimidazo[1,5-a]pyrazin-8(7H)-one Following the general procedure in Example 37, the desired product was afforded using the amine I-2G.
LC-MS (ESI, m/z)=433.0 (M+H$^+$).

Example 41: 6-(4-(2,6-Difluoro-4-(morpholinomethyl)phenyl)piperazin-1-yl)-3-methylimidazo[1,5-a]pyrazin-8(7H)-one Following the general procedure in Example 37, the desired product was afforded using the amine obtained in Preparation Example 3.
LC-MS (ESI, m/z)=445.1 (M+H$^+$).

Example 42: 6-(4-(2,6-Difluoro-4-((4-methylpiperazin-1-yl)methyl)phenyl)piperazin-1-yl)-3-methylimidazo[1,5-a]pyrazin-8(7H)-one Following the general procedure in Example 37, the desired product was afforded using the amine obtained by following a method similar to that described in Preparation Example 3.
LC-MS (ESI, m/z)=458.9 (M+H$^+$).

Example 43: 6-(4-(2,6-Difluoro-4-(oxetan-3-yloxy)phenyl)piperazin-1-yl)-3-methylimidazo[1,5-a]pyrazin-8(7H)-one Following the general procedure in Example 37, the desired product was afforded using the amine I-2D.
LC-MS (ESI, m/z)=417.7 (M+H$^+$).

Example 44: 6-(4-(2,6-Difluoro-4-(1-methoxyethyl)phenyl)piperazin-1-yl)-3-methylimidazo[1,5-a]pyrazin-8(7H)-one Following the general procedure in Example 37, the desired product was afforded using the amine obtained in Preparation Example 4.
LC-MS (ESI, m/z)=403.9 (M+H$^+$).

Example 45: 6-(4-(2,6-Difluoro-4-((2-methoxyethyl)(methyl)amino)methyl)phenyl)piperazin-1-yl)-3-methylimidazo[1,5-a]pyrazin-8(7H)-one Following the general procedure in Example 37, the desired product was afforded using the amine obtained by following a method similar to that described in Preparation Example 3.
LC-MS (ESI, m/z)=447.0 (M+H$^+$).

Example 46: 6-(4-(2,6-Difluoro-4-(2-(pyrrolidin-1-yl)ethoxy)phenyl)piperazin-1-yl)-3-methylimidazo[1,5-a]pyrazin-8(7H)-one Following the general procedure in Example 37, the desired product was afforded using the amine I-11C.
LC-MS (ESI, m/z)=459.0 (M+H$^+$).

Example 47: 6-(4-(2,6-Difluoro-4-(2-(4-methylpiperazin-1-yl)ethoxy)phenyl)piperazin-1-yl)-3-methylimidazo[1,5-a]pyrazin-8(7H)-one Following the general procedure in Example 37, the desired product was afforded using the amine I-11D.
LC-MS (ESI, m/z)=488.9 (M+H$^+$).

Example 48: 6-(4-(2,6-Difluoro-4-(3-(piperidin-1-yl)propoxy)phenyl)piperazin-1-yl)-3-methylimidazo[1,5-a]pyrazin-8(7H)-one Following the general procedure in Example 37, the desired product was afforded using the amine prepared in Example 26.
LC-MS (ESI, m/z)=487.0 (M+H$^+$).

Example 49: Analysis of activity of tankyrase 1

Activities of novel compounds synthesized according to Examples 1 to 48 against tankyrase 1 were analyzed using a Trevigen kit (Cat. No. 4700-096-K). Poly PAR histone protein-coated 96-well plate, anti-PAR monoclonal antibody and goat anti-mouse IgG-HRP were used for measurement of absorbance by ELISA method. Specifically, 20× I-PAR assay buffer was diluted to 1× by adding water, and 50 μL of the diluted buffer was added to each well of the 96-well plate followed by reacting at rt for 30 min. Then, the supernatant was completely removed from each well and 10 μL of 1× I-PAR assay buffer and 15 μL of assay substrate were added to each well along with 1 μL of a 50× solution of inhibitors to be tested, which were the compounds obtained in the Examples 1 to 48. 10 m Units/μL of tankyrase 1 enzyme was diluted 50-fold with 1× I-PAR assay buffer and 25 μL of the diluted enzyme was added to each well and reacted while stirring at rt for 30 min. One without any compound of the present invention was used as a positive control and another containing 1× I-PAR assay buffer with the same volume instead of tankyrase 1 enzyme was used as a negative control. Upon completion of the reaction, 200 μL of PBSX, which was prepared by adding 0.1% triton X-100 to PBS, was added and removed and this washing process was repeated twice. Washing was repeated twice more using PBS in the same manner. 5× antibody diluent was diluted with distilled water to 1× concentration, 50 μL of the diluted goat anti-mouse IgG-HRP to 1/2000 was added to each well and reacted while stirring at rt for 30 min. Washes were carried out twice using PBSX and PBS, respectively. After addition of 50 μL of TACS-sapphire to each well of the plate, the plate was blocked from light to react for 10 min to 15 min and the color of the reaction solution turned blue. To stop the reaction, 50 μL of 0.2N HCl was added to turn the solution yellow. Finally, the absorbance of the resulting solution was measured at 450 nm.

TABLE 1

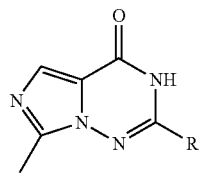

| Comp. | R group | IUPAC name | TNKS1 (IC$_{50}$) (nM) |
|---|---|---|---|
| 1 | 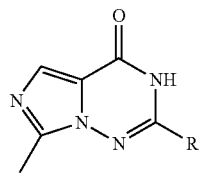 | 2-(4-(2-fluorophenyl)piperazin-1-yl)-7-methylimidazo[1,5-f][1,2,4]triazin-4(3H)-one | 109.5 |

TABLE 1-continued

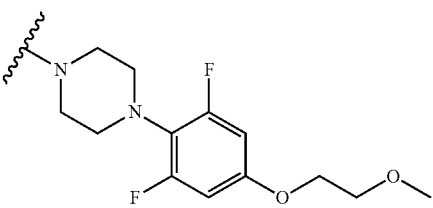 [SMILES: *N1CCN(c2c(F)cc(OCCOC)cc2F)CC1]

| Comp. | R group | IUPAC name | TNKS1 (IC$_{50}$) (nM) |
|---|---|---|---|
| 2 | 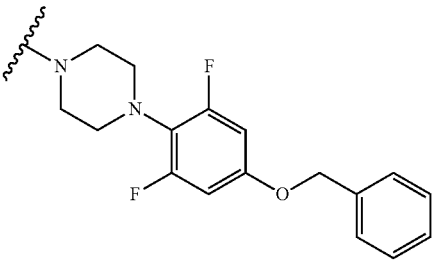 [SMILES: *N1CCN(c2c(F)cc(OCc3ccccc3)cc2F)CC1] | 2-(4-(2,6-difluoro-4-(2-methoxyethoxy)phenyl)piperazin-1-yl)-7-methylimidazo[1,5-f][1,2,4]triazin-4(3H)-one | 31.8 |
| 3 | 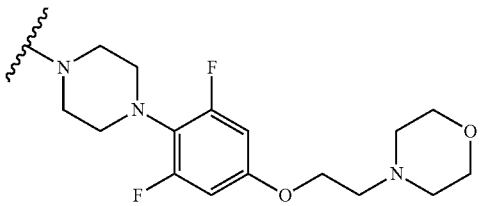 [SMILES: *N1CCN(c2c(F)cc(OCCN3CCOCC3)cc2F)CC1] | 2-(4-(4-(benzyloxy)-2,6-difluorophenyl)piperazin-1-yl)-7-methylimidazo[1,5-f][1,2,4]triazin-4(3H)-one | 494.4 |
| 4 | 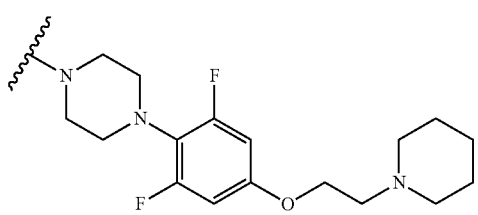 [SMILES: *N1CCN(c2c(F)cc(OCCN3CCCCC3)cc2F)CC1] | 2-(4-(2,6-difluoro-4-(2-morpholinoethoxy)phenyl)piperazin-1-yl)-7-methylimidazo[1,5-f][1,2,4]triazin-4(3H)-one | 32.3 |
| 5 | 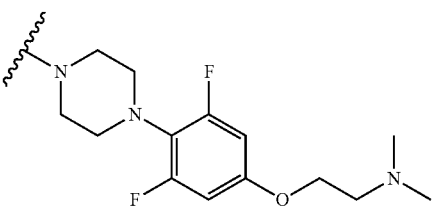 [SMILES: *N1CCN(c2c(F)cc(OCCN(C)C)cc2F)CC1] | 2-(4-(2,6-difluoro-4-(2-(piperidin-1-yl)ethoxy)phenyl)piperazin-1-yl)-7-methylimidazo[1,5-f][1,2,4]triazin-4(3H)-one | 25.2 |
| 6 | 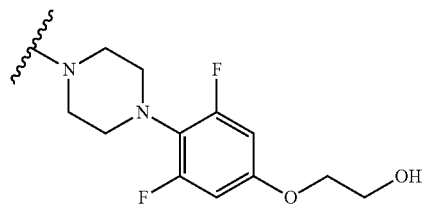 [SMILES: *N1CCN(c2c(F)cc(OCCO)cc2F)CC1] | 2-(4-(4-(2-(dimethylamino)ethoxy)-2,6-difluorophenyl)piperazin-1-yl)-7-methylimidazo[1,5-f][1,2,4]triazin-4(3H)-one | 19.6 |
| 7 |  | 2-(4-(2,6-difluoro-4-(2-hydroxyethoxy)phenyl)piperazin-1-yl)-7-methylimidazo[1,5-f][1,2,4]triazin-4(3H)-one | 38.7 |

TABLE 1-continued

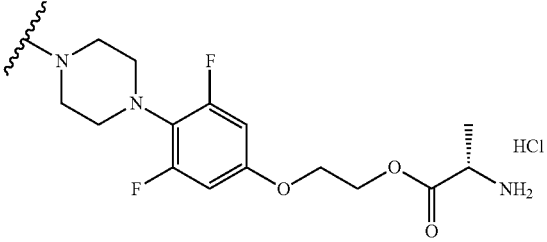 [SMILES: *N1CCN(c2c(F)cc(OCCOC(=O)[C@H](C)N)cc2F)CC1 ; Cl]

| Comp. | R group | IUPAC name | TNKS1 (IC$_{50}$) (nM) |
|---|---|---|---|
| 8 | 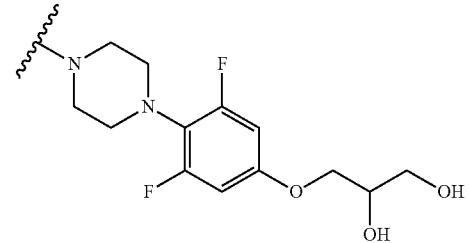 [SMILES: *N1CCN(c2c(F)cc(OCC(O)CO)cc2F)CC1] | (S)-2-(3,5-difluoro-4-(4-(7-methyl-4-oxo-3,4-dihydroimidazo[1,5-f][1,2,4]triazin-2-yl)piperazin-1-yl)phenoxy)ethyl 2-aminopropanoate hydrochloride | 43.6 |
| 9 | 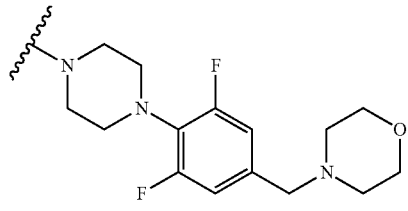 [SMILES: *N1CCN(c2c(F)cc(CN3CCOCC3)cc2F)CC1] | 2-(4-(4-(2,3-dihydroxypropoxy)-2,6-difluorophenyl)piperazin-1-yl)-7-methylimidazo[1,5-f][1,2,4]triazin-4(3H)-one | 79.5 |
| 10 | 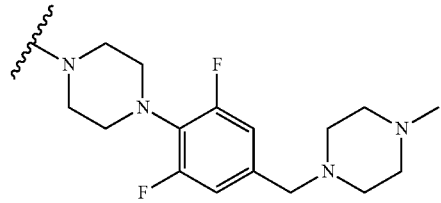 [SMILES: *N1CCN(c2c(F)cc(CN3CCN(C)CC3)cc2F)CC1] | 2-(4-(2,6-difluoro-4-(morpholinomethyl)phenyl)piperazin-1-yl)-7-methylimidazo[1,5-f][1,2,4]triazin-4(3H)-one | 48.8 |
| 11 | 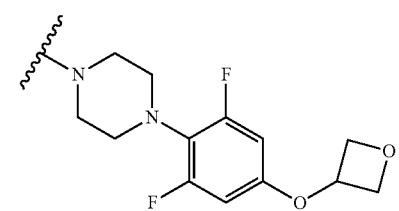 [SMILES: *N1CCN(c2c(F)cc(OC3COC3)cc2F)CC1] | 2-(4-(2,6-difluoro-4-((4-methyl piperazin-1-yl)methyl)phenyl) piperazin-1-yl)-7-methylimidazo[1,5-f][1,2,4]triazin-4(3H)-one | 44.1 |
| 12 | 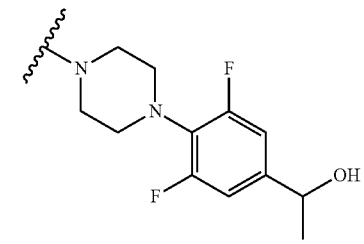 [SMILES: *N1CCN(c2c(F)cc(C(C)O)cc2F)CC1] | 2-(4-(2,6-difluoro-4-(oxetan-3-yloxy)phenyl)piperazin-1-yl)-7-methylimidazo[1,5-f][1,2,4]triazin-4(3H)-one | 96.3 |
| 13 | | 2-(4-(2,6-difluoro-4-(1-hydroxyethyl)phenyl)piperazin-1-yl)-7-methylimidazo[1,5-f][1,2,4]triazin-4(3H)-one | 45.7 |

TABLE 1-continued

| Comp. | R group | IUPAC name | TNKS1 (IC$_{50}$) (nM) |
|---|---|---|---|
| 14 | | 2-(4-(2,6-difluoro-4-(1-methoxyethyl)phenyl)piperazin-1-yl)-7-methylimidazo[1,5-f][1,2,4]triazin-4(3H)-one | 69.2 |
| 15 | | 2-(4-(2,6-difluorophenyl) piperazin-1-yl)-7-methylimidazo [1,5-f][1,2,4]triazin-4(3H)-one | 17.9 |
| 17 | | 2-(4-(2,6-difluoro-4-(2-methoxy ethoxy)phenyl)-4-hydroxypiperidin-1-yl)-7-methylimidazo[1,5-f][1,2,4] triazin-4(3H)-one | 67.2 |
| 19 | | 2-(4-(2,6-difluoro-4-(((2-methoxy ethyl)(methyl)amino)methyl)phenyl) piperazin-1-yl)-7-methylimidazo [1,5-f][1,2,4]triazin-4(3H)-one | 101.6 |
| 24 | | 2-(4-(2,6-difluoro-4-(2-(pyrrolidin-1-yl)ethoxy)phenyl)piperazin-1-yl)-7-methylimidazo[1,5-f][1,2,4] triazin-4(3H)-one | 93.44 |
| 25 | | 2-(4-(2,6-difluoro-4-(2-(4-methyl piperazin-1-yl)ethoxy)phenyl) piperazin-1-yl)-7-methylimidazo [1,5-f][1,2,4]triazin-4(3H)-one | 69.92 |

TABLE 1-continued

| Comp. | R group | IUPAC name | TNKS1 (IC$_{50}$) (nM) |
|---|---|---|---|
| 28 | | 2-(4-(2,6-difluoro-4-(2-oxo-2-(piperidin-1-yl)ethoxy)phenyl)piperazin-1-yl)-7-methylimidazo[1,5-f][1,2,4]triazin-4(3H)-one | 63.1 |
| 29 | | 2-(4-(2,6-difluoro-4-(2-oxo-2-(pyrrolidin-1-yl)ethoxy)phenyl)piperazin-1-yl)-7-methylimidazo[1,5-f][1,2,4]triazin-4(3H)-one | 84.85 |
| 31 | | 2-(4-(4-(2-azidoethoxy)-2,6-difluorophenyl)piperazin-1-yl)-7-methylimidazo[1,5-f][1,2,4]triazin-4(3H)-one | 171.4 |
| 33 | | 2-(4-(2,6-difluoro-4-(2-(4-methyl-2-oxopiperazin-1-yl)ethoxy)phenyl)piperazin-1-yl)-7-methylimidazo[1,5-f][1,2,4]triazin-4(3H)-one | 179.6 |
| 34 | | 2-(4-(4-(2-(4-aminopiperadin-1-yl)ethoxy)-2,6-difluorophenyl)piperazin-1-yl)-7-methylimidazo[1,5-f][1,2,4]triazin-4(3H)-one | 60.54 |
| 35 | | 2-(4-(2,6-difluoro-4-(2-(3-hydroxypyrrolidin-1-yl)ethoxy)phenyl)piperazin-1-yl)-7-methylimidazo[1,5-f][1,2,4]triazin-4(3H)-one | 101.7 |

TABLE 1-continued

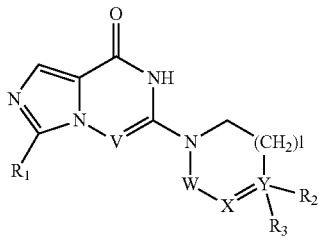

| Comp. | R group | IUPAC name | TNKS1 ($IC_{50}$) (nM) |
|---|---|---|---|
| 36 | | 2-(4-(2,6-difluoro-4-(2-(4-hydroxypiperidin-1-yl)ethoxy)phenyl)piperazin-1-yl)-7-methyl imidazo[1,5-f][1,2,4]triazin-4(3H)-one | 65.23 |

The invention claimed is:

1. A compound represented by Chemical Formula 1, a tautomer thereof, a stereoisomer thereof and their mixture, or a pharmaceutically acceptable salt thereof:

[Chemical Formula 1]

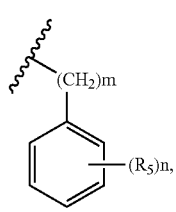

wherein

V is N or CH;
$R_1$ is hydrogen, $C_{1-6}$ alkyl, $C_{1-6}$ hydroxyalkyl, or $C_{1-6}$ dihydroxyalkyl;
each of W and X is independently $CHR_4$ or CO;
Y is N or C;
=== is a single bond or a double bond, determined by X and Y;
l is 0, 1 or 2;
$R_2$ is none, hydrogen, hydroxyl, cyano or $C_{1-6}$ alkyl;
$R_3$ is heteroaryl, heteroaryl-$C_{1-3}$ alkyl, heterocyclyl, or heterocyclyl $C_{1-3}$ alkyl;
$R_4$ is none, hydrogen, hydroxyl, $C_{1-6}$ alkyl or amine;
m is 0, 1, 2 or 3;
n is 0, 1, 2, 3, 4 or 5;
each of $R_5$ is independently halo, $C_{1-6}$ alkyl, $C_{2-6}$ alkenyl, $C_{1-6}$ alkoxy, $C_{1-3}$ alkoxy-$C_{1-3}$ alkyl, $C_{1-6}$ hydroxyalkyl, $C_{1-6}$ dihydroxyalkyl, $C_{1-6}$ haloalkyl unsubstituted or optionally substituted with hydroxy, $C_{3-7}$ cycloalkyl, $C_{1-6}$ alkyloxo, cyano, nitro, carboxy, $C_{1-6}$ alkoxycarbonyl or —Z—$(CH_2)_p$—$R_6$;
p is 0, 1, 2, 3, 4, 5 or 6;
Z is —O—, —S(O)$_q$—, —$CONR_7$—, —$CHR_7$— or none;
q is 0, 1 or 2;
$R_6$ is hydrogen, cyano, hydroxyl, azido, $C_{1-6}$ alkoxy, $C_{1-3}$ alkoxy-$C_{1-3}$ alkyl, $C_{5-10}$ aryl, carboxy, $C_{1-6}$ dihydroxyalkyl, $C_{1-6}$ alkyl, $C_{1-6}$ haloalkyl unsubstituted or optionally substituted with hydroxy, $C_{3-6}$ cycloalkyl, heterocyclyl, heteroaryl, —S(O)$_r$—$R_8$, —O—(C=O)—$R_8$, —(C=O)—$R_8$, —$OR_8$, —$COOR_8$, —$NR_9R_{10}$ or —(C=O)$NR_9R_{10}$;
r is 0, 1 or 2;
$R_7$ is hydrogen, $C_{1-6}$ alkyl, $C_{3-6}$ cycloalkyl, $C_{1-3}$ alkyl-$C_{3-6}$ cycloalkyl or $C_{1-3}$ alkoxy-$C_{1-3}$ alkyl;
$R_8$ is hydrogen, $C_{1-6}$ alkyl, $C_{1-6}$ alkoxy, amino, $C_{1-6}$ alkylamino, $C_{1-6}$ aminoalkyl, heterocyclyl, $C_{3-6}$ cycloalkyl, $C_{1-3}$ alkyl-$C_{3-6}$ cycloalkyl, $C_{1-6}$ alkyloxo or $C_{1-3}$ alkoxy-$C_{1-3}$ alkyl;
each of $R_9$ and $R_{10}$ is independently hydrogen, $C_{1-6}$ alkyl, $C_{1-6}$ alkoxy, $C_{3-6}$ cycloalkyl, $C_{1-3}$ alkyl-$C_{3-6}$ cycloalkyl, $C_{1-3}$ alkoxy-$C_{1-3}$ alkyl or —(SO$_2$)—$C_{1-3}$ alkyl;
each of the heteroaryls may be a 5- to 10-membered single or fused ring containing one or more heteroatom selected from the group consisting of N, O, S and a combination thereof, and each of the heterocycles may be a 3- to 10-membered single or fused ring containing one or more heteroatom selected from the group consisting of N, O, S and a combination thereof;
each of the cycloalkyls and heterocyclyls may optionally be substituted with one to three substituents selected from the group consisting of $C_{1-6}$ alkyl, hydroxyl, oxo, $C_{1-6}$ hydroxyalkyl, halo, cyano, nitro, $C_{1-6}$ haloalkyl, $C_{1-6}$ alkoxy, formyl, $C_{1-6}$ alkylformyl, carboxy, $C_{1-6}$ alkylcarboxy, amino, $C_{1-6}$ alkylamino, di($C_{1-6}$ alkyl) amino, carbamoyl, $C_{1-6}$ alkylcarbamoyl, di($C_{1-6}$ alkyl) carbamoyl and $C_{1-3}$ alkoxy-$C_{1-3}$ alkyl; and
each of the aryls and heteroaryls may optionally be substituted with one to three substituents selected from the group consisting of $C_{1-6}$ alkyl, $C_{1-6}$ alkoxy, $C_{1-3}$ alkoxy-$C_{1-3}$ alkyl, $C_{1-6}$ hydroxyalkyl, $C_{1-6}$ haloalkyl, halo, cyano, pyrazinyl, hydroxy, oxo, nitro, formyl, $C_{1-6}$ alkylformyl, carboxy, $C_{1-6}$ alkylcarboxy, amino, $C_{1-6}$ alkylamino, di($C_{1-6}$ alkyl)amino, carbamoyl, $C_{1-6}$ alkylcarbamoyl, di($C_{1-6}$ alkyl)carbamoyl and $C_{1-6}$ alkylsulfonyl.

2. The compound according to claim 1,
wherein
V is N or CH;
$R_1$ is hydrogen, $C_{1-6}$ alkyl, $C_{1-6}$ hydroxyalkyl, or $C_{1-6}$ dihydroxyalkyl;
each of W and X is independently CH or $CH_2$;
Y is N or C;
=== is a single bond or a double bond; and
l is 0, 1 or 2,
a tautomer thereof, a stereoisomer thereof and their mixture, or a pharmaceutically acceptable salt thereof.

3. The compound according to claim 1,
wherein
V is N or CH;
$R_1$ is hydrogen or $C_{1-6}$ alkyl;
each of W and X is independently CH or $CH_2$;
Y is N or C;
=== is a single bond or a double bond;
l is 0, 1 or 2;
$R_2$ is none, hydrogen or hydroxyl;
$R_3$ is

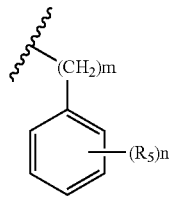

or heteroaryl;
$R_4$ is none or hydrogen;
m is 0;
n is 1, 2 or 3;
each of $R_5$ is independently halo, $C_{2-6}$ alkenyl, $C_{1-6}$ alkoxy, $C_{1-3}$ alkoxy-$C_{1-3}$ alkyl, $C_{1-6}$ hydroxyalkyl, $C_{1-6}$ dihydroxyalkyl or —Z—$(CH_2)_p$—$R_6$;
p is 0, 1, 2, 3 or 5;
Z is —O—, —$NR_7$— or none;
$R_6$ is cyano, hydroxyl, azido, $C_{1-6}$ alkoxy, $C_{1-3}$ alkoxy-$C_{1-3}$ alkyl, $C_{5-10}$ aryl, carboxy, $C_{1-6}$ dihydroxyalkyl, $C_{1-6}$ haloalkyl unsubstituted or optionally substituted with hydroxy, heterocyclyl, heteroaryl, —S(O)$_r$—$R_8$, —O—(C=O)—$R_8$, —(C=O)—$R_8$, —$NR_9R_{10}$ or —(C=O)$NR_9R_{10}$;
r is 2;
$R_7$ is hydrogen;
$R_8$ is hydrogen, $C_{1-6}$ alkyl, $C_{1-6}$ alkoxy, amino, $C_{1-6}$ alkylamino, $C_{1-6}$ aminoalkyl or heterocyclyl;
each of $R_9$ and $R_{10}$ is independently hydrogen, $C_{1-6}$ alkyl, $C_{1-3}$ alkoxy-$C_{1-3}$ alkyl or —(SO$_2$)—$C_{1-3}$ alkyl;
each of the heteroaryls may be a 5- to 10-membered single or fused ring containing one or more heteroatom selected from the group consisting of N, O, S and a combination thereof, and each of the heterocycles may be a 3- to 10-membered single or fused ring containing one or more heteroatom selected from the group consisting of N, O, S and a combination thereof;
each of the heterocyclyls may optionally be substituted with one to three substituents selected from the group consisting of $C_{1-6}$ alkyl, hydroxyl, amino, oxo, $C_{1-6}$ hydroxyalkyl and halo; and
each of the heteroaryls may optionally be substituted with one to three $C_{1-6}$ alkyl,
a tautomer thereof, a stereoisomer thereof and their mixture, or a pharmaceutically acceptable salt thereof.

4. The compound according to claim 1,
wherein
V is N or CH;
$R_1$ is hydrogen or methyl;
each of W and X is independently CH or $CH_2$;
Y is N or C;
=== is a single bond or a double bond;
l is 1 or 2;
$R_2$ is none, hydrogen or hydroxyl;
$R_3$ is

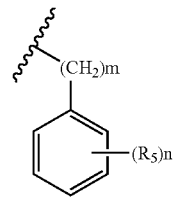

or heteroaryl;
$R_4$ is none or hydrogen;
m is 0;
n is 1, 2 or 3;
each of $R_5$ is independently fluoro, vinyl, isopropoxy, methoxyethyl, methoxypropyl, hydroxyethyl, 1,2-dihydroxyethyl, 2,3-dihydroxypropyl or —Z—$(CH_2)_p$—$R_6$;
p is 0, 1, 2, 3 or 5;
Z is —O—, —$NR_7$— or none;
$R_6$ is cyano, hydroxyl, azido, methoxy, ethoxy, methoxyethyl, $C_{5-10}$ aryl, carboxy, 1,2-dihydroxyethyl, 1-chloro-3-hydroxyisopropyl, perfluoromethyl, heterocyclyl, heteroaryl, —S(O)$_r$—$R_8$, —O—(C=O)—$R_8$, —(C=O)—$R_8$, —$NR_9R_{10}$ or —(C=O)$NR_9R_{10}$;
r is 2;
$R_7$ is hydrogen;
$R_8$ is hydrogen, methyl, amino, methylamino, or aminoethyl;
each of $R_9$ and $R_{10}$ is independently hydrogen, methyl, ethyl or methoxyethyl;
each of the heteroaryls may be a 5- to 10-membered single or fused ring containing one or more heteroatom selected from the group consisting of N, O, S and a combination thereof, and each of the heterocycles may be a 3- to 10-membered single or fused ring containing one or more heteroatom selected from the group consisting of N, O, S and a combination thereof;
each of the heterocyclyls may optionally be substituted with one to three substituents selected from the group consisting of methyl, fluoro, hydroxyl, amino and oxo; and
each of the heteroaryls may optionally be substituted with one to three methyls,
a tautomer thereof, a stereoisomer thereof and their mixture, or a pharmaceutically acceptable salt thereof.

5. The compound according to claim 4,
wherein
each of the aryls is phenyl or naphthyl;
each of the heteroaryls may be selected from the group consisting of tetrazolyl, imidazolyl, pyridinyl, pyridazinyl, pyrimidyl, triazinyl, pyrrolyl, pyrazolyl, triazolyl, pyrazinyl, furyl, thienyl, isoxazolyl, thiazolyl, isothiazolyl, thiadiazolyl, furazanyl, oxazolyl, indolyl, isoindolyl, indazolyl, quinolinyl, isoquinolinyl, benzothiazolyl, benzoxazolyl, benzofuranyl, benzoimidazolyl, benzotriazolyl and azaindolyl; and
each of the heterocyclyls may be selected from the group consisting of tetrahydropyranyl, tetrahydrofuranyl, dihydrofuranyl, dihydropyranyl, dioxanyl, dithianyl, dioxolanyl, imidazolidinyl, imidazolinyl, pyrrolinyl, oxetanyl, pyrrolidinyl, piperidinyl, piperazinyl, morpholinyl, thiomorpholinyl, dioxothiomorpholinyl, dioxotetrahydrothiophenyl, dioxothiolanyl, oxopiperidinyl, oxopyrrolidinyl and oxo-oxazolidinyl,
a tautomer thereof, a stereoisomer thereof and their mixture, or a pharmaceutically acceptable salt thereof.

6. The compound according to claim 5,
wherein
each of the aryls is phenyl;
each of the heteroaryls is tetrazolyl or imidazolyl; and
each of the heterocyclyls is tetrahydrofuranyl, oxetanyl, pyrrolidinyl, piperidinyl, piperazinyl or morpholinyl,
a tautomer thereof, a stereoisomer thereof and their mixture, or a pharmaceutically acceptable salt thereof.

7. The compound according to claim 6,
wherein
each of the heterocyclyls is tetrahydrofuranyl, oxetanyl, pyrrolidinyl, piperidinyl, piperazinyl, morpholinyl, 4-methylpiperazinyl, 4-methyl-2-oxopiperazinyl, 3-hydroxypyrrolidinyl, 2-hydroxymethylpyrrolidinyl, N-methylpyrrolidinyl, 4-hydroxypiperidinyl, 4-hydroxy-4-methylpiperidinyl, 4-aminopiperidinyl, 2-oxopiperidinyl, 2,6-dimethylpiperidinyl or 4,4-difluoropiperidinyl,
a tautomer thereof, a stereoisomer thereof and their mixture, or a pharmaceutically acceptable salt thereof.

8. The compound according to claim 1,
wherein the compound is selected from the group consisting of
1) 2-(4-(2-fluorophenyl)piperazin-1-yl)-7-methylimidazo[1,5-f][1,2,4]triazin-4(3H)-one,
2) 2-(4-(2,6-difluoro-4-(2-methoxyethoxy)phenyl)piperazin-1-yl)-7-methylimidazo[1,5-f][1,2,4]triazin-4(3H)-one,
3) 2-(4-(4-(benzyloxy)-2,6-difluorophenyl)piperazin-1-yl)-7-methylimidazo[1,5-f][1,2,4]triazin-4(3H)-one,
4) 2-(4-(2,6-difluoro-4-(2-morpholinoethoxy)phenyl)piperazin-1-yl)-7-methylimidazo[1,5-f][1,2,4]triazin-4(3H)-one,
5) 2-(4-(2,6-difluoro-4-(2-(piperidin-1-yl)ethoxy)phenyl)piperazin-1-yl)-7-methylimidazo[1,5-f][1,2,4]triazin-4(3H)-one,
6) 2-(4-(4-(2-(dimethylamino)ethoxy)-2,6-difluorophenyl)piperazin-1-yl)-7-methylimidazo[1,5-f][1,2,4]triazin-4(3H)-one,
7) 2-(4-(2,6-difluoro-4-(2-hydroxyethoxy)phenyl)piperazin-1-yl)-7-methylimidazo[1,5-f][1,2,4]triazin-4(3H)-one,
8) (S)-2-(3,5-difluoro-4-(4-(7-methyl-4-oxo-3,4-dihydroimidazo[1,5-f][1,2,4]triazin-2-yl)piperazin-1-yl)phenoxy)ethyl 2-aminopropanoate hydrochloride,
9) 2-(4-(4-(2,3-dihydroxypropoxy)-2,6-difluorophenyl)piperazin-1-yl)-7-methylimidazo[1,5-f][1,2,4]triazin-4(3H)-one,
10) 2-(4-(2,6-difluoro-4-(morpholinomethyl)phenyl)piperazin-1-yl)-7-methylimidazo[1,5-f][1,2,4]triazin-4(3H)-one,
11) 2-(4-(2,6-difluoro-4-((4-methylpiperazin-1-yl)methyl)phenyl)piperazin-1-yl)-7-methylimidazo[1,5-f][1,2,4]triazin-4(3H)-one,
12) 2-(4-(2,6-difluoro-4-(oxetan-3-yloxy)phenyl)piperazin-1-yl)-7-methylimidazo[1,5-f][1,2,4]triazin-4(3H)-one,
13) 2-(4-(2,6-difluoro-4-(1-hydroxyethyl)phenyl)piperazin-1-yl)-7-methylimidazo[1,5-f][1,2,4]triazin-4(3H)-one,
14) 2-(4-(2,6-difluoro-4-(1-methoxyethyl)phenyl)piperazin-1-yl)-7-methylimidazo[1,5-f][1,2,4]triazin-4(3H)-one,
15) 2-(4-(2,6-difluorophenyl)piperazin-1-yl)-7-methylimidazo[1,5-f][1,2,4]triazin-4(3H)-one,
16) 2-(4-(2,4,6-trifluorophenyl)piperazin-1-yl)-7-methylimidazo[1,5-f][1,2,4]triazin-4(3H)-one,
17) 2-(4-(2,6-difluoro-4-(2-methoxyethoxy)phenyl)-4-hydroxypiperidin-1-yl)-7-methylimidazo[1,5-f][1,2,4]triazin-4(3H)-one,
18) 2-(4-(2,6-difluoro-4-(2-methoxyethylamino)phenyl)piperazin-1-yl)-7-methylimidazo[1,5-f][1,2,4]triazin-4(3H)-one,
19) 2-(4-(2,6-difluoro-4-(((2-methoxyethyl)(methyl)amino)methyl)phenyl)piperazin-1-yl)-7-methylimidazo[1,5-f][1,2,4]triazin-4(3H)-one,
20) 2-(4-(4-(1,2-dihydroxyethyl)-2,6-difluorophenyl)piperazin-1-yl)-7-methylimidazo[1,5-f][1,2,4]triazin-4(3H)-one,
21) 2-(4-(4-(2,3-dihydroxypropyl)-2,6-difluorophenyl)piperazin-1-yl)-7-methylimidazo[1,5-f][1,2,4]triazin-4(3H)-one,
22) 2-(4-(1H-tetrazol-5-yl)piperidin-1-yl)-7-methylimidazo[1,5-f][1,2,4]triazin-4(3H)-one,
23) 7-methyl-2-(4-(2-methyl-2H-tetrazol-5-yl)piperidin-1-yl)imidazo[1,5-f][1,2,4]triazin-4(3H)-one,
24) 2-(4-(2,6-difluoro-4-(2-(pyrrolidin-1-yl)ethoxy)phenyl)piperazin-1-yl)-7-methylimidazo[1,5-f][1,2,4]triazin-4(3H)-one,
25) 2-(4-(2,6-difluoro-4-(2-(4-methylpiperazin-1-yl)ethoxy)phenyl)piperazin-1-yl)-7-methylimidazo[1,5-f][1,2,4]triazin-4(3H)-one,
26) 2-(4-(2,6-difluoro-4-(3-(piperidin-1-yl)propoxy)phenyl)piperazin-1-yl)-7-methylimidazo[1,5-f][1,2,4]triazin-4(3H)-one,
27) 2-(4-(4-(bis(2-methoxyethyl)amino)-2,6-difluorophenyl)piperazin-1-yl)-7-methylimidazo[1,5-f][1,2,4]triazin-4(3H)-one,
28) 2-(4-(2,6-difluoro-4-(2-oxo-2-(piperidin-1-yl)ethoxy)phenyl)piperazin-1-yl)-7-methylimidazo[1,5-f][1,2,4]triazin-4(3H)-one,
29) 2-(4-(2,6-difluoro-4-(2-oxo-2-(pyrrolidin-1-yl)ethoxy)phenyl)piperazin-1-yl)-7-methylimidazo[1,5-f][1,2,4]triazin-4(3H)-one,
30) 2-(4-(4-(2-(4-aminopiperidin-1-yl)ethoxy)-2,6-difluorophenyl)-1,4-diazepan-1-yl)-7-methylimidazo[1,5-f][1,2,4]triazin-4(3H)-one,
31) 2-(4-(4-(2-azidoethoxy)-2,6-difluorophenyl)piperazin-1-yl)-7-methylimidazo[1,5-f][1,2,4]triazin-4(3H)-one, 32) 2-(4-(4-(2-aminoethoxy)-2,6-difluorophenyl)piperazin-1-yl)-7-methylimidazo[1,5-f][1,2,4]triazin-4(3H)-one,
33) 2-(4-(2,6-difluoro-4-(2-(4-methyl-2-oxopiperazin-1-yl)ethoxy)phenyl)piperazin-1-yl)-7-methylimidazo[1,5-f][1,2,4]triazin-4(3H)-one,
34) 2-(4-(4-(2-(4-aminopiperidin-1-yl)ethoxy)-2,6-difluorophenyl)piperazin-1-yl)-7-methylimidazo[1,5-f][1,2,4]triazin-4(3H)-one,
35) 2-(4-(2,6-difluoro-4-(2-(3-hydroxypyrrolidin-1-yl)ethoxy)phenyl)piperazin-1-yl)-7-methylimidazo[1,5-f][1,2,4]triazin-4(3H)-one,
36) 2-(4-(2,6-difluoro-4-(2-(4-hydroxypiperidin-1-yl)ethoxy)phenyl)piperazin-1-yl)-7-methylimidazo[1,5-f][1,2,4]triazin-4(3H)-one,
37) 6-(4-(2,6-difluoro-4-(2-methoxyethoxy)phenyl)piperazin-1-yl)-3-methylimidazo[1,5-a]pyrazin-8(7H)-one,
38) 6-(4-(2,6-difluoro-4-(2-morpholinoethoxy)phenyl)piperazin-1-yl)-3-methylimidazo[1,5-a]pyrazin-8(7H)-one,
39) 6-(4-(2,6-difluoro-4-(2-(piperidin-1-yl)ethoxy)phenyl)piperazin-1-yl)-3-methylimidazo[1,5-a]pyrazin-8(7H)-one,
40) 6-(4-(4-(2-(dimethylamino)ethoxy)-2,6-difluorophenyl)piperazin-1-yl)-3-methylimidazo[1,5-a]pyrazin-8(7H)-one,
41) 6-(4-(2,6-difluoro-4-(morpholinomethyl)phenyl)piperazin-1-yl)-3-methylimidazo[1,5-a]pyrazin-8(7H)-one,
42) 6-(4-(2,6-difluoro-4-((4-methylpiperazin-1-yl)methyl)phenyl)piperazin-1-yl)-3-methylimidazo[1,5-a]pyrazin-8(7H)-one,
43) 6-(4-(2,6-difluoro-4-(oxetan-3-yloxy)phenyl)piperazin-1-yl)-3-methylimidazo[1,5-a]pyrazin-8(7H)-one,
44) 6-(4-(2,6-difluoro-4-(1-methoxyethyl)phenyl)piperazin-1-yl)-3-methylimidazo[1,5-a]pyrazin-8(7H)-one,
45) 6-(4-(2,6-difluoro-4-(((2-methoxyethyl)(methyl)amino)methyl)phenyl)piperazin-1-yl)-3-methylimidazo[1,5-a]pyrazin-8(7H)-one,
46) 6-(4-(2,6-difluoro-4-(2-(pyrrolidin-1-yl)ethoxy)phenyl)piperazin-1-yl)-3-methylimidazo[1,5-a]pyrazin-8(7H)-one,
47) 6-(4-(2,6-difluoro-4-(2-(4-methylpiperazin-1-yl)ethoxy)phenyl)piperazin-1-yl)-3-methylimidazo[1,5-a]pyrazin-8(7H)-one, and
48) 6-(4-(2,6-difluoro-4-(3-(piperidin-1-yl)propoxy)phenyl)piperazin-1-yl)-3-methylimidazo[1,5-a]pyrazin-8(7H)-one, a tautomer thereof, a stereoisomer thereof and their mixture, or a pharmaceutically acceptable salt thereof.

9. A pharmaceutical composition comprising the compound according to claim 1, or a tautomer thereof, a stereoisomer thereof or a mixture thereof, or a pharmaceutically acceptable salt thereof as an active ingredient, together with at least one pharmaceutically acceptable carrier, diluent, or excipient.

\* \* \* \* \*